United States Patent [19]
Millan

[11] Patent Number: 5,773,226
[45] Date of Patent: Jun. 30, 1998

[54] RECOMBINANT CALF INTESTINAL ALKALINE PHOSPHATASE

[75] Inventor: Jose L. Millan, San Diego, Calif.

[73] Assignee: La Jolla Cancer Research Foundation, La Jolla, Calif.

[21] Appl. No.: 458,181

[22] Filed: Jun. 2, 1995

Related U.S. Application Data

[63] Continuation of Ser. No. 368,071, Jan. 3, 1995, Pat. No. 5,707,853, which is a continuation of Ser. No. 213,371, Mar. 14, 1994, abandoned, which is a continuation of Ser. No. 849,219, Mar. 10, 1992, abandoned.

[51] Int. Cl.$^6$ .......................... G01N 33/53; C12Q 1/42; C12N 9/16
[52] U.S. Cl. .................. 435/7.9; 435/6; 435/7.1; 435/21; 435/196
[58] Field of Search .............................. 435/196, 6, 7.1, 435/21, 7.9; 935/47; 530/402

[56] References Cited

U.S. PATENT DOCUMENTS

| | | | |
|---|---|---|---|
| 4,707,438 | 11/1987 | Keydar | 435/5 |
| 5,047,507 | 9/1991 | Buchegger et al. | 530/387 |
| 5,055,415 | 10/1991 | Imai et al. | 436/516 |
| 5,071,761 | 12/1991 | Meyer et al. | 435/243 |
| 5,079,141 | 1/1992 | Niskanen et al. | 435/7.34 |
| 5,079,170 | 1/1992 | Rosman et al. | 436/178 |
| 5,079,171 | 1/1992 | Senyei et al. | 436/510 |
| 5,084,379 | 1/1992 | Calenoff et al. | 435/7.1 |
| 5,089,424 | 2/1992 | Khalil et al. | 436/518 |
| 5,204,244 | 4/1993 | Fell et al. | 435/69.6 |

OTHER PUBLICATIONS

Berger et al., "Cloning and Sequencing of Human Intestinal Alkaline Phosphatase cDNA." Proc. Natl. Acad. Sci. USA 84:695–698 (1987).

Culp et al., "The Active–Site and Amino–Terminal Amino Acid Sequence of Bovine Intestinal Alkaline Phosphatase." Biochem. Biophys. Acta. 830:330–334 (1985).

Eliakim et al., "Differential Regulation of mRNAs Encoding for Rat Intestinal Alkaline Phosphatase." Am. J. Physiol. 259:G93–98 (1990).

Besman, M., and Coleman, J.E., "Isozymes of Bovine Intestinal Alkaline Phosphatase," J. Biol. Chem. 260:11190–11193 (1985).

Culp et al., "The active–site and amino–terminal amino acid sequence of bovine intestinal alkaline phosphatase," Biochem. Biophys. Acta 831:330–334 (1985).

Garattini et al., "Cloning and sequencing of bovine kidney alkaline phosphatase cDNA," Gene 59:41–46 (1987).

Hahnel et al., "Two alkaline phosphatase genes are expressed during early development in the mouse embryo," Development 110:555–564 (1990).

Henthorn et al., "Sequence and Characterization of the Human Intestinal Alkaline Phosphatase Gene," J. Biol. Chem. 263:12011–12019 (1988).

Hoylaerts, M.F., and Millan, J.L., "Site–directed mutagenesis and epitope–mapped monoclonal antibodies define a catalytically important conformational difference between human placental and germ cell alkaline phosphatase," Eur. J. Biochem. 202:605–616 (1991).

Hummer, C., and Millan, J.L., "Gly$^{429}$ is the major determinant of uncompetitive inhibition of human germ cell alkaline phosphatase by L–leucine," Biochem. J. 274:91–95 (1991).

Knoll et al., "Nucleotide Sequence of the Human Placental Alkaline Phosphatase Gene," J. Biol. Chem. 263:12020–12027 (1988).

Low, M.G., and Saltiel, A.R., "Structural and Functional Roles of Glycosyl–Phosphatidylinositol in Membranes," Science 239:268–275 (1988).

Manes et al., "Genomic Structure and Comparison of Mouse Tissue–Specific Alkaline Phosphatase Genes," Genomics 8:541–554 (1990).

Millan, J.L., and Manes, T., "Seminoma–derived Nagao isozyme is encoded by a germ–cell alkaline phosphatase gene," Proc. Natl. Acad. Sci. USA 85:3024–3028 (1988).

Millan, J.L., "Promoter structure of the human intestinal alkaline phosphatase gene," Nucl. Acids. Res. 15:10599 (1987).

Millan, J.L., "Oncodevelopmental Expression and Structure of Alkaline Phosphatase Genes," Anticancer Res. 8:995–1004 (1988).

Millan, J.L., in Prog. Clin. Biol. Res., "Oncodevelopmental Alkaline Phosphatases: In Search for a Function," 344:453–475 (1990).

Milstein, C., "The Amino Acid Sequence Around the Reactive Serine Residue in Alkaline Phosphatase from Escherichia coli," Biochem. J. 92:410–422 (1964).

Tsonis et al., "A putative functional domain of human placental alkaline phosphatase predicted from sequence comparisons," Biochem. J. 254:623–624 (1988).

Weissig et al. J. Biochem. v. 290, pp. 503–508, 1993.

Besman et al., J. Biol Chem., 260: 11190–93, 1985.

Primary Examiner—Keith D. Hendricks
Attorney, Agent, or Firm—Campbell & Flores LLP

[57] ABSTRACT

The invention relates to isolated nucleic acids encoding recombinant calf intestinal alkaline phosphatase. Expression vectors and host cells transformed or transfected with such vectors are also provided. The invention further provides multifunctional polypeptides containing amino acid sequences encoding for calf intestinal alkaline phosphatase and a second amino acid sequence encoding a reagent having specific reactivity with a ligand. The recombinant calf intestinal alkaline phosphatase or its active fragments and the multifunctional polypeptides can be used in the methods for determining the presence or concentration of a ligand.

12 Claims, 7 Drawing Sheets

FIG. 1A

```
GGT GTA ATG GCA GCC GCC CGC TAC AAC CAG TGC AAA ACG ACA CGT GGG AAT GAG GTC ACG TCT GTG ATG AAC CGG GCC AAG AAA GCA G GT  2355
Gly Val Ser Ala Ala Ala Arg Tyr Asn Gln Cys Lys Thr Thr Arg Gly Asn Glu Val Thr Ser Val Met·Asn Arg Ala Lys Lys Ala G

GGGCTTGGGCGTCAGCTTCCTGGGCAGGGACGGGCTCAGAGACCTCAGTGGCCCACCGTGACCTCTGCCACCCTCAG GG AAG TCC GTG GGA GTG GTG ACC ACC ACC AGG  2464
                                                                               ly Lys Ser Val Gly Val Val Thr Thr Thr Arg

GTG CAG CAT GCC TCC CCA GCC GGG GCC TAC GCG CAC ACG GTG AAC CGA AAC TGG TAC TCA GAC GCC GAC CTG CCT GCT GAT GCA CAG ATG  2554
Val Gln His Ala Ser Pro Ala Gly Ala Tyr Ala His Thr Val Asn Arg Asn Trp Tyr Ser Asp Ala Asp Leu Pro Ala Asp Ala Gln Met

AAT GGC TGC CAG GAC ATC GCC GCA CAG CTG GTC AAC AAC ATG GAT ATT GAC GTGCGACATGTTGGGCACAGGGCGGGGCTGGGCACAGCTGGTGGGGCACACT  2657
Asn Gly Cys Gln Asp Ile Ala Ala Gln Leu Val Asn Asn Met Asp Ile Asp

CGCAACACAGTCGTAGGTAACCTCCAGCCTGCGGTGTTTCAGGGTTTTCATGGGTTTGTGTGTGTGTGTATGTGTGGTGGGGTGGCACCATGTAGGAGGTGGCCACAGGCCTTTCCCACA  2777

GACCTGGTGGGGCAGGTAGGGGCTGTGTGAGAGGAGTAAAGGGCCAGCCAGGCCCCTAACCCACCTGCCTAACTCTCTGGCTCCAG GTG ATC CTG GGT GCA GGC CGA AAA  2887
                                                                                       Val Ile Leu Gly Gly Gly Arg Lys

TAC ATG TTT CCT GTG GGG ACC CCA GAC CCT GAA TAC CCA GAT GAT GCC AGT GTG AAT GGA GTC CGG AAG CGA AAG CAG AAC CTG GTG CAG  2977
Tyr Met Phe Pro Val Gly Thr Pro Asp Pro Glu Tyr Pro Asp Asp Ala Ser Val Asn Gly Val Arg Lys Arg Lys Gln Asn Leu Val Gln

GCA TGG CAG GCC AAG CAC CAG GTAATGGGGGCTCACGGATGTGGGGGTACAGTGGGGCTGGGCCTGGGGTGTCGGCTATGGCTGAGGCCTGGTTCTGCCCTCCCAG GGA  3086
Ala Trp Gln Ala Lys His Gln                                                                                     Gly

GCC CAG TAT GTG TGG AAC CGC ACT GCG CTC CTT CAG GCG CCC GAT GAC TCC AGT GTA ACA CAC CTC ATG G GTAACGACTCCACCCACCCTCACTGT  3182
Ala Gln Tyr Val Trp Asn Arg Thr Ala Leu Leu Gln Ala Ala Asp Asp Ser Ser Val Thr His Leu Met G

CCTCCCCAGGAATGGGTGCCATGGGCCACCCCTGTCCTCAGCTTGACGGTCACCACTGCTCCCCTTTCCCACAG GC CTC TTT GAG CCG GCA GAC ATG AAG TAT AAT  3288
                                                                            ly Leu Phe Glu Pro Ala Asp Met Lys Tyr Asn

GTT CAG CAA GAC CAC ACC AAG GAC CCG ACC CTG CAG GAA ATG ACA GAG GTG GCC CTG CGA GTC GTA AGC AGG AAC CCC AGG GGC TTC TAC  3378
Val Gln Gln Asp His Thr Lys Asp Pro Thr Leu Gln Glu Met Thr Glu Val Ala Leu Arg Val Val Ser Arg Asn Pro Arg Gly Phe Tyr

CTC TTT GTG GAG G GTGAGTGGCAGCCCCTTGGTGAACAGAGGTGTGATGAGGGCCATCAGGGTGGGTTTGGTATCTTATATGTGACTTATCTGCAG GA GGC CGC ATT GAC  3488
Leu Phe Val Glu G                                                                                      ly Gly Arg Ile Asp
```

```
A A Q A L D V A K K L Q P I Q T A A K N V I L F L G D    42    b.IAP
- K E - - - - - - - - - - - - - - S - - - L - - - - - -   42    r.IAP
- - E - - - A - - - - - - - - - - S - - - L - I - - - -   42    m.IAP
- - E - - - A - - - - - - - - - K V - - - L - - - - - -   42    h.IAP

A L S K T Y H V D R Q V P D S A G T A T A Y L C G V K   104    b.IAP
- - - - - - S - - - - - - - - S - - - - - - - - - - -   104    r.IAP
- - - - - - S - - - - - - - - S - - - - - - - - - - -   104    m.IAP
- - - - - - - - - - - - - - - A - - - - - - - - - - -   104    h.IAP

G K S V G V V T T T R V Q H A S P A G A Y A H T V H R   166    b.IAP
- - - - - - - - - - - - - - - - - - T - - - - - - - -   166    r.IAP
- - - - - - - - - - - - - - - - S - T - V - - - - - -   166    m.IAP
- - - - - - - - - - - - - - - - - - T - - - - - - - -   166    h.IAP

G G R K Y M F P V G T P D P E Y P D D A S V N G V R K   228    b.IAP
- - - - - F - - - K - - - - - - - - G - S D Q S - - - L   228    r.IAP
- - - - - - - - - A M - - - - - - - H - - N E T - T - L   228    m.IAP
- - - - - - - - - M - - - - - - - - A - - - Q - - I - L   228    h.IAP

H L M G L F E P A D M K Y H V Q Q D H T K D P T L Q E   290    b.IAP
R - - - - - - - T E - - - D - H R N A S A - - S - A -   290    r.IAP
Y - - - - - - - V - T - F D I - R - P L M - - S - K D   290    m.IAP
- - - - - - - - G - T - - E I H R - P - L - - S - M -   290    h.IAP

M A L T E A G M F D H A I A K A H E L T S E L D T L I   352    b.IAP
L - - - - - - V - - - S - - E - - S Q - - H - K - - - T   352    r.IAP
L - - - - - - V - - - L - - E R - S Q - - - - R - - - T   352    m.IAP
Q - - - - - - V - - - D - - E R - G Q - - - - E - - - T   352    h.IAP

Y T S I L Y G N G P G Y A L G G G S R P D V H D S T S   414    b.IAP
- - - - - - - - - - - - V - N S - H - - N - T - A E -   414    r.IAP
- - - - - - - - - - - V G - T - E - - N - T A A E -     413    m.IAP
- - - T - - - - - - - V F H S - V - - - - - E S E -     414    h.IAP

H G V E E E T F V A H I M A F A G C V E P Y T D C H L   476    b.IAP
- - - Q - Q H Y I - - V - - - - - - L - - - - - - G -   476    r.IAP
- - - Q - Q H Y I - - V - - S - - - L - - - - - - G -   475    m.IAP
- - - Q - Q S - - - - V - - - - A - L - - - - A - D -   476    h.IAP

T L Y                                                   514    b.IAP
L V G T A L V V S                                       520    r.IAP
A R S L G P A T A P L A L A L L A G M L M L L L G A P A E  540    m.IAP
                                                        508    h.IAP
```

FIG. 3B

RECOMBINANT CALF INTESTINAL ALKALINE PHOSPHATASE

This application is a continuation of application Ser. No. 08/368,071, filed Jan. 3, 1995, now U.S. Pat. No. 5,707,853, which is a continuation of U.S. Ser. No. 08/213,371, filed Mar. 14, 1994, now abandoned which is a continuation of U.S. Ser. No. 07/849,219, filed Mar. 10, 1992 now abandoned.

The invention was made, in part, with government support under grants CA48560 and CA30199 awarded by the National Institutes of Health. The United States government has certain rights in this invention.

BACKGROUND OF THE INVENTION

The present invention relates to recombinant calf intestinal alkaline phosphatase and more particularly to isolated nucleic acids encoding the recombinant form of calf intestinal alkaline phosphatase.

Alkaline phosphatases (APs) are a family of functionally related enzymes named after the tissues in which they predominately appear. Such enzymes carry out hydrolase/transferase reactions on phosphate-containing substrates at a high pH optimum. The exact role of APs in biological processes remains poorly defined.

In humans and other higher animals, the AP family contains four members that are each encoded by a separate gene locus as reviewed in Millan, Anticancer Res. 8:995–1004 (1988) and Harris, Clin. Chem. Acta 186:133–150 (1989). The alkaline phosphatase family includes the tissue specific APs (placental AP, germ cell AP and intestinal AP) and the tissue non-specific AP found predominately in the liver, bone and kidney.

Intestinal alkaline phosphatase (IAP) derived from humans has been extensively characterized. As with all known APs, human IAP appears as a dimer, which is referred to as p75/150 in Latham & Stanbridge, P.N.A.S. (USA) 87:1263–1267 (1990). A cDNA clone for human adult IAP has been isolated from a λgt11 expression library. This cDNA clone is 2513 base pairs in length and contains an open reading frame that encodes a 528 amino acid polypeptide as described in Henthorn et al., P.N.A.S. (USA) 84:1234–1238 (1987). IAP has also been found in other species, such as mice, cows, and fish as reported in McComb et al., Alkaline Phosphatases (Plenum, New York, 1989).

Generally, alkaline phosphatases are useful diagnostically in liver and bone disorders as described in McComb et al., supra, or for certain cancers as reviewed in Millan, Prog. Clin. Biol. Res., 344:453–475 (1990). APs are also useful as reagents in molecular biology. Of the known APs, bovine IAP has the highest catalytic activity. This property has made bovine IAP highly desirable for such biotechnological applications as enzyme-conjugates for use as diagnostics reagents or dephosphorylation of DNA, for example.

The isozymes of bovine IAP (b.IAP), including calf IAP, adult bovine IAP, and a tissue non-specific isozyme extracted from the small intestines, have been characterized by Besman & Coleman, J. Biol. Chem., 15 260:1190–1193 (1985). Although it is possible to purify naturally-occurring calf IAP extracted from intestinal tissues, it is technically very difficult to obtain an enzyme preparation of reproducible quality and purity. Generally, the enzymes are extracted from bovine intestines obtained from slaughter houses. Since the sacrificed animals are not of the same age, the proportion of the known b.IAP isozymes will vary significantly among the purified extracts.

Moreover, the intestine is known to contain high amounts of peptidases and glycosidases that degrade the naturally occurring IAP. Since the time from slaughter to enzyme extraction varies greatly, the amount of degradation will also vary greatly, resulting in a mixture of intact and several degradation products. Accordingly, the known methods of purifying IAP from naturally-occurring sources produce microheterogeneity in the purified IAP preparations. These partially degraded IAP molecules are technically difficult to separate from the native intact IAP molecules.

Due in part to the technical problems of separating intact b.IAP from degraded or partially processed calf IAP and the minute quantities of purified intact b.IAP that can be obtained from naturally-occurring sources, it has been difficult to determine the amino acid sequence encoding calf IAP. In addition, attempts to crystalize the IAP protein to determine the three-dimensional structure from the natural source has been hampered because of such microheterogeneity of the enzyme obtained from natural sources. It has only been possible to obtain small crystals of the natural enzyme, which are of insufficient quality for crystallographic studies.

Thus, a need exists for a homogeneous source of calf intestine alkaline phosphatase. Such a source would ideally provide an ample supply of pure, intact calf IAP for research and commercial use without time-consuming and labor intensive procedures. The present invention satisfies this need and provides related advantages as well.

SUMMARY OF THE INVENTION

The present invention generally relates to recombinant calf intestinal alkaline phosphatase (calf IAP) having an amino acid sequence substantially the same as naturally occurring calf IAP or its active fragments. The invention further provides isolated nucleic acids encoding such polypeptides. Vectors containing these nucleic acids and recombinant host cells transformed or transfected with such vectors are also provided.

Nucleic acid probes having nucleotide sequences complementary to a portion of the nucleotide sequence encoding calf IAP are also provided. Such probes can be used for the detection of nucleic acids encoding calf IAP or active fragments thereof.

The present invention further provides a multifunctional polypeptide containing an amino acid sequence of calf IAP and a second amino acid sequence having specific reactivity with a desired ligand. The second amino acid sequence can encode, for example, an antibody sequence when the desired ligand is an antigen.

The pure recombinant polypeptides of the present invention, including the multifunctional polypeptides, are particularly useful in methods for detecting the presence of antigens or other ligands in substances, such as fluid samples and tissues. Such diagnostic methods can be used for in vitro detection of such ligands.

BRIEF DESCRIPTION OF THE DRAWINGS

FIG. 1 shows the full length genomic sequence (SEQ ID NO: 9) of calf IAP and the deduced amino acid sequence (SEQ ID NO: 10).

FIG. 3 shows a comparison of IAPs from calf (b.IAP; SEQ ID NO: 10), rat (r.IAP; SEQ ID NO: 11), mouse (m.IAP; SEQ ID NO: 12), and human (h.IAP; SEQ ID NO: 13).

DETAILED DESCRIPTION OF THE INVENTION

Figure 2:
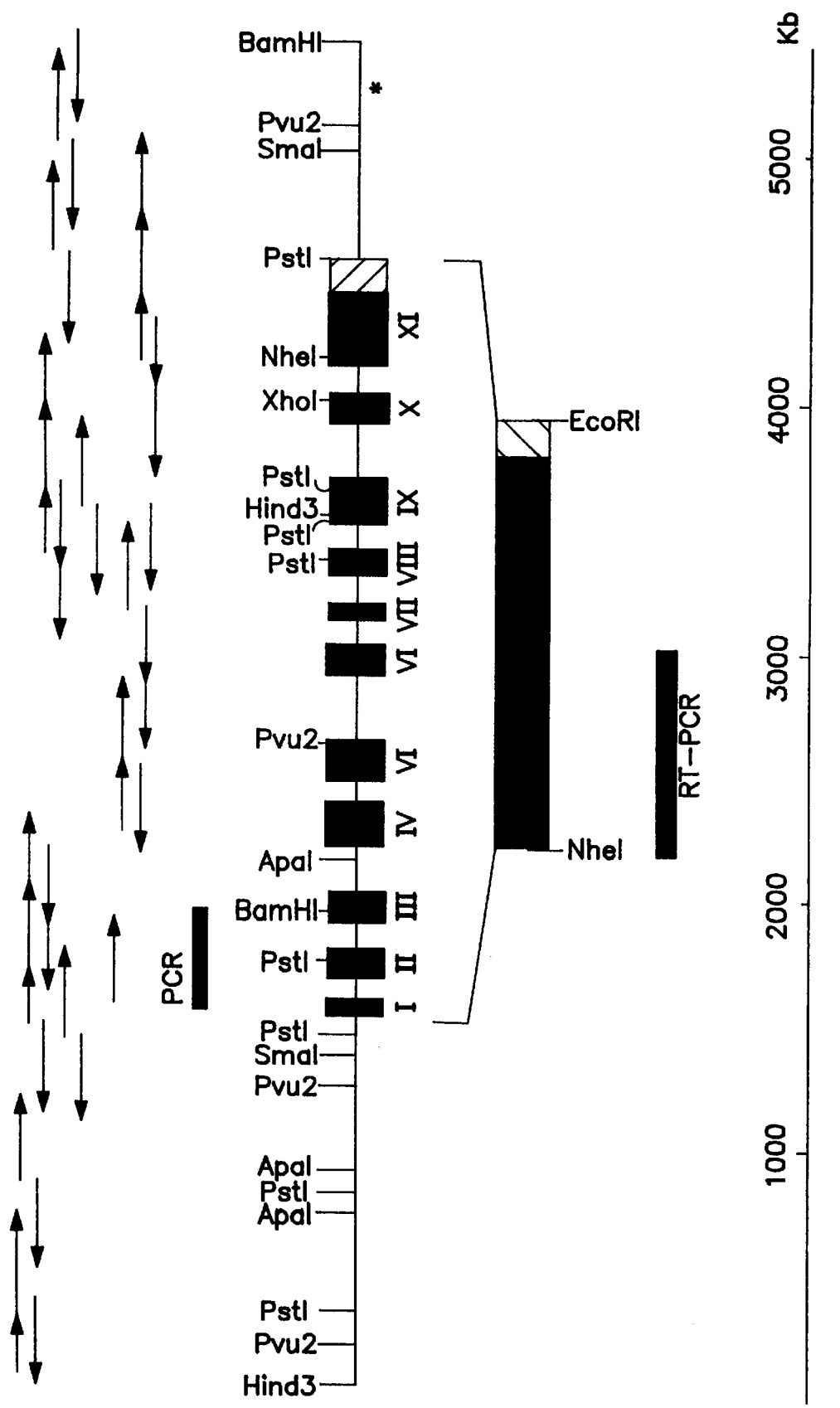
FIG. 2 shows the restriction map of the entire calf IAP gene and the full length cDNA.

The present invention relates to the elucidation of the calf intestinal alkaline phosphatase gene. More. specifically, the invention relates to the nucleotide sequence of the region of the gene encoding the enzyme.

Previous attempts to produce a full length cDNA or a complete genomic clone for calf IAP have been unsuccessful. RNA extracted from bovine intestinal tissues are not fully processed (i.e., incompletely spliced RNA) or are quickly degraded after death. As such, only fragments of the genome coding region could be obtained.

It was through the extensive experimentation as set forth in the examples below that the full length cDNA clone of calf IAP was determined. Accordingly, the present invention is directed to isolated nucleic acids comprising the nucleotide sequence encoding calf IAP or an active fragment thereof having the enzymatic activity of the intact calf IAP. The nucleic acids can be DNA, cDNA or RNA.

Figure 1A:
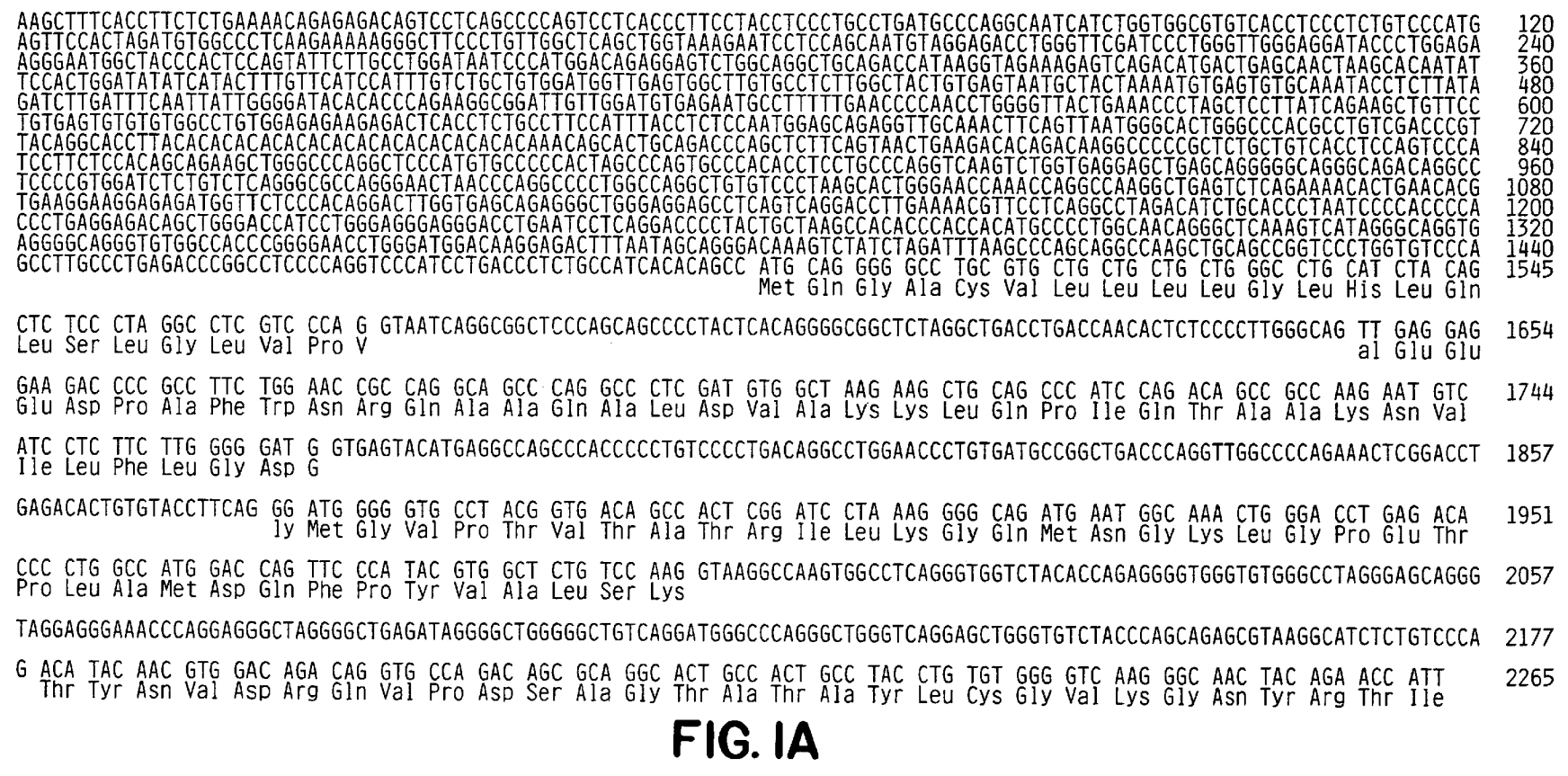
Figure 1C:
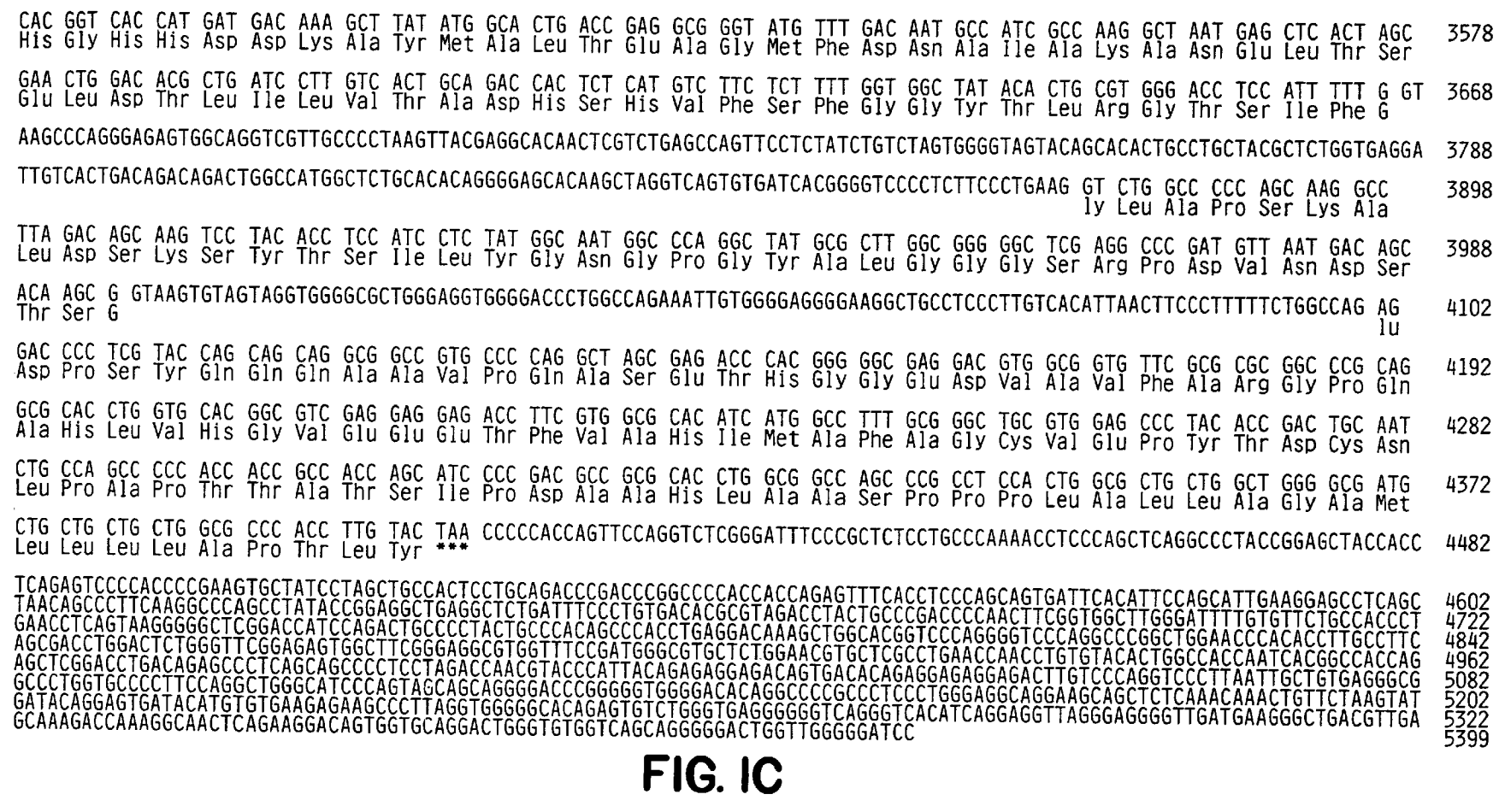

The nucleic acid can have the nucleotide sequence substantially the same as the sequence identified in FIG. 1, which shows the complete coding region of the genomic sequence of calf IAP. This nucleic acid (5.4 kb) contains 11 exons separated by 10 small introns at positions identical to those of other members of the tissue-specific AP family. Additionally, a 1.5 kb of the 5' sequence contains putative regulatory elements having homology to human and mouse IAP promoter sequences.

As used herein, the term "substantially the sequence" means the described nucleotide or amino acid sequence or other sequences having one or more additions, deletions or substitutions that do not substantially affect the ability of the sequence to encode a polypeptide having a desired activity, such as calf IAP or its active fragments. Thus, modifications that do not destroy the encoded enzymatic activity are contemplated.

As used herein, an active fragment of calf IAP refers to portions of the intact enzyme that substantially retains the enzymatic activity of the intact enzyme. The retention of activity can be readily determined using methods known to those skilled in the art.

The terms "isolated" and "substantially purified" are used interchangeably and mean the polypeptide or nucleic acid is essentially free of other biochemical moieties with which it is normally associated in nature. Recombinant polypeptides are generally considered to be substantially purified.

The present invention further relates to expression vectors into which the coding region of the calf IAP gene can be subcloned. "Vectors" as used herein are capable of expressing nucleic acid sequences when such sequences are operationally lined to other sequences capable of effecting their expression. These expression vectors must be replicable in the host organisms either as episomes or as an integral part of the chromosomal DNA. Lack of replicability would render them effectively inoperable. In general, useful vectors in recombinant DNA techniques are often in the form of plasmids, which refer to circular double stranded DNA loops which are not bound to the chromosome in their vector form. Suitable expression vectors can be plasmids such as, for example, pcDNAl (Invitrogen, San Diego, Calif.).

A number of procaryotic expression vectors are known in the art, such as those disclosed, for example, in U.S. Pat. Nos. 4,440,859; 4,436,815; 4,431,740; 4,431,739; 4,428,941; 4,425,437; 4,418,149; 4,411,994 and 4,342,832, all incorporated herein by reference. Eucaryotic systems and yeast expression vectors can also be used as described, for example, in U.S. Pat. Nos. 4,446,235; 4,443,539; and 4,430,428, all incorporated herein by reference.

The vectors can be used to transfect or transform suitable host cells by various methods known in the art, such as described in Sambrook et al., *Molecular Cloning: A Laboratory Manual,* Cold Spring Harbor, N.Y. (1989). Such host cells can be either eucaryotic or procaryotic cells. Examples of such hosts include chinese hamster ovary (CHO) cells, E.Coli and baculovirus infected insect cells. As used herein, "host cells" or "recombinant host cells" refer not only to the particular subject cell but to the progeny or potential progeny of such cell. Because certain modifications may occur in succeeding generations due to either mutation or environmental influences, such progeny may not, in fact, be identical to the parent cell, but are still included within the scope of the term as used herein.

The present invention further relates to recombinant proteins or polypeptides produced by the recombinant host cells of the present invention. The recombinant calf IAP protein has been characterized in terms of its heat stability up to about 50° C., electrophoretic and isoelectric focusing (IEF) behavior and kinetic parameters. The recombinant calf IAP protein of the present invention demonstrated displayed kinetic properties comparable to commercially available purified calf IAP, while showing less heterogenicity than the commercial enzymes in polyacrylamide gel electrophoresis and IEF, as described in the examples below.

Methods for obtaining or isolating recombinant calf IAP or active fragments are also provided. Such methods include culturing the recombinant host cells in a suitable growth medium. The protein or active fragments can thereafter be isolated from the cells by methods known in the art. If the expression system secretes calf IAP protein into growth media, the protein can be purified directly from cell-free media. If the protein is not secreted, it can be isolated from cell lysates. The selection of the appropriate growth conditions and recovery methods are within the knowledge of one skilled in the art. Recombinant calf IAP or active fragments thereof can be unglycosylated or have a different glycosylation pattern than the native enzyme depending on the host that is used to prepare it.

The present invention further provides isolated nucleic acids containing a nucleotide sequence encoding calf IAP or an active fragment thereof and a second nucleotide sequence encoding a polypeptide having specific reactivity with a ligand. Such nucleic acids encode a chimeric or multifunctional polypeptide in which a region of the polypeptide has enzymatic activity conferred by the calf IAP sequence attached to a second region having specific reactivity with a particular ligand. Such multifunctional polypeptides are particularly useful in diagnostic assays for determining the presence or concentration of a particular ligand in a sample. The ligand can be, for example, a cancer marker, allergen, drug or other moiety having an ability to specifically bind with an antibody or antibody-like agent encoded by a multifunctional polypeptide of the present invention. For instance, the second nucleotide sequence can encode an anti-CEA antibody when the target ligand is CEA (carcinoembryonic antigen). The ligand can also be a fragment of DNA or other nucleic acids.

Nucleic acid probes specific for a portion of nucleotides that encode calf IAP can be used to detect nucleic acids specific to calf IAP for diagnostic purposes. Nucleic acid probes suitable for such purposes can be prepared from the cloned sequences or by synthesizing oligonucleotides that hybridize only with the homologous sequence under stringent conditions. The oligonucleotides can be synthesized by any appropriate method, such as by an automated DNA synthesizer.

The oligonucleotides can be used to detect DNA and mRNA or to isolate CDNA clones from libraries. The particular nucleotide sequences selected are chosen so as to correspond to the codons encoding a known amino acid sequence from the protein. Generally, an effective length of a probe is recognized in the art is about 14 to about 20 bases. Longer probes of about 25 to about 60 bases can also used. A probe can be labelled, using labels and methods well known in the art, such as a radionucleotide or biotin, using standard procedures.

The purified recombinant calf IAP or its active fragments can be used for diagnostic purposes to determine the presence or concentration of a ligand in a sample. The sample can be a fluid or tissue specimen obtained, for example, from a patient suspected of being exposed to a particular antigen or DNA fragment. Those skilled in the art will recognize that any assay capable of using an enzyme-catalyzed system can be used in the detection methods of the present invention.

In the detection methods of the present invention:
(a) a sample is contacted with the recombinant calf IAP or an active fragment thereof attached to a reagent specifically reactive with the ligand to be detected;
(b) the sample is contacted with a detectable agent catalyzed by calf IAP; and
(c) the binding of the sample to the reagent is detected, where binding indicates the presence of the ligand in the sample.

The methods can also be used to determine the concentration of a ligand in the sample by relating the amount of binding to the concentration of the ligand. To etermine the concentration, the amount of binding can be compared to known concentrations of the ligand or to standardized measurements, such as slopes, determined from known concentrations of the ligand.

A variety of ligands can be detected by the present methods. The ligand can be, for example, a protein or polypeptide having antigenic properties or a nucleic acid, such as DNA or RNA.

Reagents reactive with such ligands can be antibodies or reactive fragments of such antibodies when the ligand is an antigen or antigen-like molecule. The reagent can also be a nucleotide probe that hybridizes or binds to a specific nucleic acid, such as DNA or RNA. Such probes can be oligonucleotides that are complementary to CDNA or genomic fragments of a ligand.

Procedures for attaching the enzymes to various reagents are well known in the art. Techniques for coupling enzymes to antibodies, for example, are described in Kennedy et al., *Clin. Chim. Acta* 70:1 (1976), incorporated herein by reference. Reagents useful for such coupling include, for example, glutaraldehyde, p-toluene diisocyanate, various carbodiimide reagents, p-benzoquinone m-periodate, N,N'-o-phenylenediamalemide and the like. Alternatively, the multifunctional polypeptides of the present invention can be used.

Suitable substrates for the biochemical detection of ligands according to the methods of the present invention include, for example, p-nitrophenylphosphate.

The recombinant form of calf IAP is also useful for the development of calf IAP having greater heat stability. By site directed mutagenesis, it is possible to modify the nucleic acid sequence encoding for the recombinant protein to obtain a heat stable calf IAP comparable to human placental IAP, which is known to be stable at about 65° C. Greater heat stability would allow the use of such a modified calf IAP in procedures requiring higher heating, such as Southern blotting, for example, which generally denatures many enzymes.

The following examples are intended to illustrate but not limit the invention.

EXAMPLE I

Libraries and Screening Procedures

Initially, a γgtll CDNA library prepared from adult bovine intestine (Clontech Laboratories, Palo Alto, Calif.) was screened using a mouse IAP CDNA fragment described in Manes et al., *Genomics* 8:541–554 (1990) as a probe. A 2.1 kb unprocessed CDNA fragment and a 1.1 kb processed CDNA fragment, both isolated from this library, were used to screen a genomic library prepared from adult cow liver in EMBL3 SP6/T7 (Clontech Laboratories, Palo Alto, Calif.). Radiolabelling of probes with $^{32}$P and identification and isolation of positive clones was done as described in Manes et al., supra, which is incorporated herein by reference. Large-scale phage DNA preparation was performed as described in Sambrook et al.,supra, incorporated herein by reference.

Initially, one positive cDNA clone was obtained upon screening the λgt11 cDNA library with the mouse IAP CDNA fragment. Sequencing from the ends of the 2.1 kb cDNA fragment (R201) revealed an incomplete cDNA encoding exons VI through XI of an alkaline phosphatase gene as identified by sequence comparison to known AP genes. This cDNA fragment included all introns and revealed several STOP codons as well as two frameshifts in the putative coding region of the gene.

Although further sequence information of R201 suggested that it is possibly transcribed from a pseudogene, it was used as a probe for further screening of the γgtll library. Two additional CDNA clones were subsequently isolated and identified as transcripts of another alkaline phosphatase gene. Again, one fragment of 0.8 kb length (BB203) turned out to be reverse transcribed from an incomplete and unprocessed RNA, whereas the other one, a cDNA fragment of 1.1 kb length (BB204), was derived from a partial but processed mRNA, extending from the end of exon V through exon XI, lacking a putative poly-adenylation site and a poly-A tail.

EXAMPLE II

Characterization of Genomic Clones and Sequence Analysis

Genomic DNA was isolated from adult cow liver and Southern blot analysis was performed using standard protocols as described in Sambrook et al., supra. Restriction enzymes were obtained from Gibco BRL, Boehringer Mannheim, and New England Biolabs. Twenty μg of genomic DNA were used per reaction. The blots were probed with the 2.1 kb unprocessed cDNA fragment, and washed under high stringency conditions (0.1×SSC at 65° C.).

Two bands in the genomic Southern were identified as fragments derived from the b.IAP gene. The only other non-human mammalian genome investigated extensively for tissues specific (TSAP) genes so far has been the murine genome, as reported in Manes et al., supra. Two murine TSAP genes, one termed embryonic AP (EAP), the other coding for IAP, and a pseudogene were cloned. In previous studies, it was shown that there are two TSAP genes expressed in the bovine genome according to Culp et al., *Biochem. Biophys. Acta* 831:330–334 (1985) and Besman & Coleman, supra. Similarly, two APs have been found expressed in the adult intestine of mice as reported in Hahnel et al., *Development* 110:555–564 (1990). Expression of AP in rat intestine appears to be even more complex (Ellakim et al., *Am. J. Physiol.* 159, 1.1:G93–98 (1990)). Identification of the b.IAP gene was possible by comparison of its deduced amino acid sequence with N-terminal sequences reported for both TSAP isozymes.

Since further screening of the CDNA library revealed no additional positive clones, both R201 and BB204 were used to screen an EMBL3 SP6/T7 genomic library. Three positive clones were obtained and analyzed by Southern blotting. Subsequent sequencing of several fragments from two of the clones showed that one contained the entire coding region for the b.IAP gene as identified by comparison of deduced amino acid sequence with sequences previously determined in Culp et al., supra and Besman & Coleman, supra. A 5.4 kb sequence from overlapping Hind III and BamHl fragments of the clone containing the b.IAP gene are presented in FIG. 1. The other clone contained sequences identical (except for a few basepair changes) with R201.

Genomic clones were characterized and sequences were determined as described in Manes et al., supra. Nucleic acid and protein sequences were assembled and analyzed using the MacVector sequence analysis program (IBI, New Haven, Conn.).

EXAMPLE III

PCR Mutagenesis and Subcloning into RcDNA

A 23-mer primer ("MKNHE (SEQ ID NO: 1)":5'-GCTAGCCATGCAGGGGGCCTGCG-3'(SEQ ID NO: 2)) was used to amplify base pairs 1497–1913 of the b.IAP gene which had been subcloned as a Hind III/BamHl fragment into Bluescript-KS+ (Stratagene, San Diego, Calif.). MKNHE (SEQ ID NO: 1) had been designed to create a new Nhe I site by altering the three 5' nucleotides of the primer sequence compared to the genomic sequence to allow the easy subcloning into different expression vectors. The universal SK primer was used as complementary reverse primer in the performed polymerase chain reaction (PCR). The plasmid was heat denatured, annealed to the primers and subjected to 30 cycles of PCR amplification in an Automatic Thermocycler (MJ Research, Piscataway, N.J.). Times and temperatures were set as follows: annealing at 40° C. for 30 seconds, extension for 3 minutes at 72° C. and denaturing at 95° C. for 30 seconds. The amplified fragment was directly subcloned into the "T-modified" EcoRV site of Bluescript as described in Marchuk et al., Nucl. Acids Res. 19:1154 (1990), incorporated herein by reference, in the orientation of b-galactosidase transcription.

EXAMPLE IV

Sequencing of the Amplified Fragmnent

The amplified fragment was sequenced using the universal T3 and T7 primers in the Sanger dideoxy chain termination procedure as described in Sanger et al., *Proc. Natl. Acad. Sci. U.S.A.* 74:5463–5467 (1977), which is incorporated herein by reference, to exclude the possibility of secondary mutations. The Hind III/BamHl fragment was used together with a 3.2 kb BamHl/Smal fragment of the b.IAP gene for directional subcloning into a Hind III/EcoRV opened pe DNA 1 expressiqon vector (Invitrogen, San Diego, Calif.).

EXAMPLE V

Recombinant Expression of b.IAP

The b.IAP gene subcloned into pcDNA 1 was transfected into Chinese hamster ovary (CHO) cells, ATCC No. CCL61, by means of $Ca^{2+}$ coprecipitation as described in Hummer and Millan, *Biochem. J.* 274:91–95 (1991), which is incorporated herein by reference. The recombinant protein was extracted with butanol after incubating for 2 days.

The b.IAP gene presented in FIG. 1 includes an open reading frame (ORF) of 2946 bp, containing 11 exons and 10 introns of very compact nature. Exon and intron borders were determined by comparison with BB204 and other known AP genes described in Manes et al., gran, Hernthorn et al., *J. Biol. Chem.* 263:12011–12019 (1988), Knoll et al., *J. Biol. Chem.* 63:12020–12027 (1988), and Millan & Manes, *Proc. Natl. Acad. Sci. USA* 85:3025–3028 (1988). A translation initiation codon ATG was identified by sequence comparison to known TSAP genes and is preceded by an in-frame STOP codon 48 bp upstream. The ORF, which is terminated by the STOP codon TAA, codes for a peptide of 533 amino acids in length. The mature protein of 514 amino acids with a calculated $M_r$ of 64,400 Da is preceded by a hydrophobic signal peptide as is the case for all known APs.

Figure 3A:
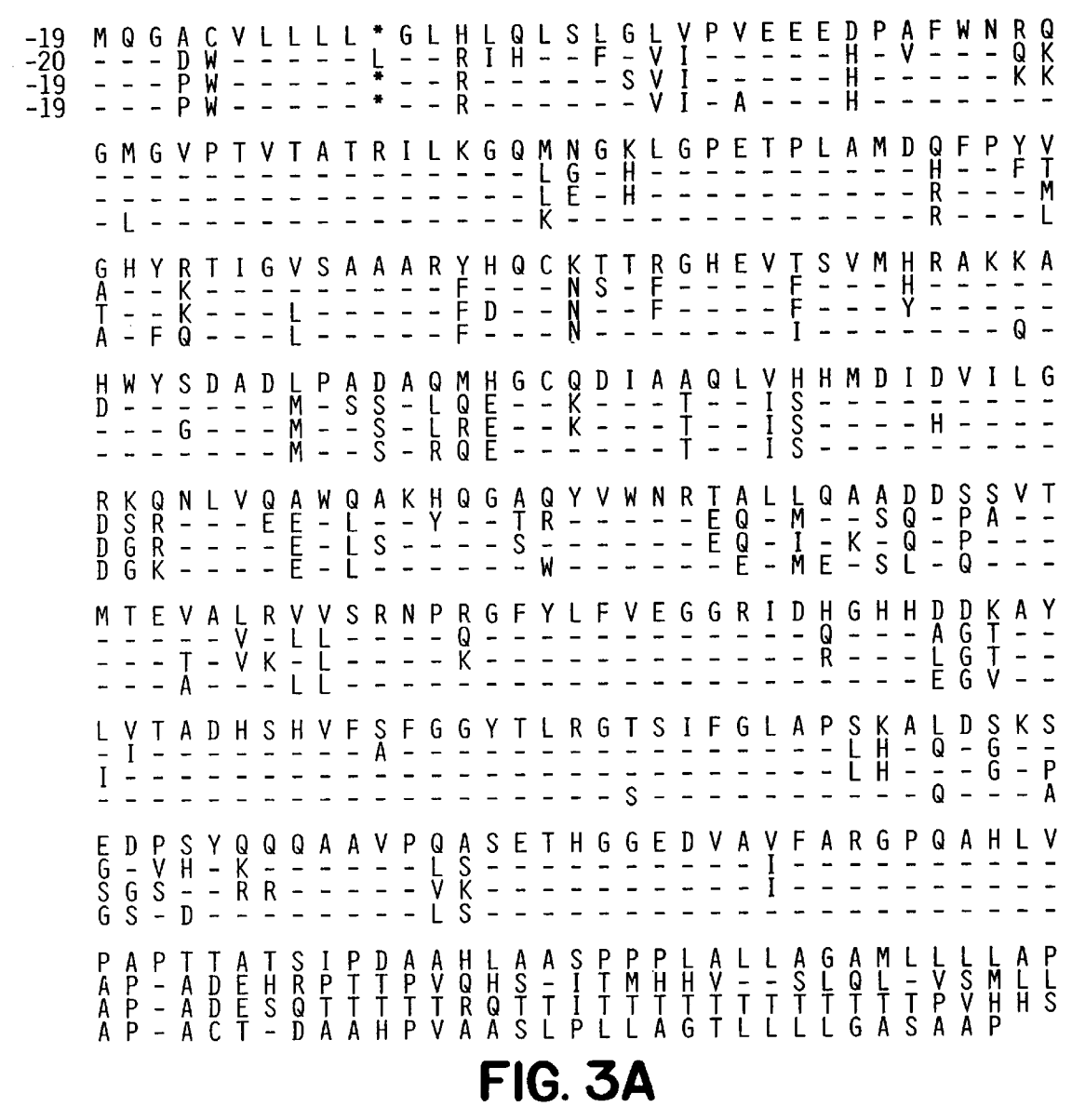

The predicted amino acid sequence of the b.IAP protein is highly honologous to other known IAPs as shown in FIG. 3. As shown in FIG. 3 there is identity in those parts corresponding to the partial amino acid sequences previously determined for b.IAP (Culp et al., supra; Besman and Coleman, supra). Besman & Coleman determined N-terminal amino acid sequences for two differentially expressed AP isozymes. The 16 N-terminal amino acids determined for the isozyme found only in newborn calves differ in three or four residues from the N-terminus of the enzyme exclusively expressed in adults.

EXAMPLE VI

Reverse Transcritase-PCR

In order to construct a full length cDNA, reverse ranscriptase-PCR (RT-PCR) was performed as follows: total NA from a stable transfected CHO-cell clone (M2) was isolated by acid guanidium thiocyanate-phenol-chloroform extraction as described in Chomozynski & Sacchi, *Anal. Biochem.* 162:156–159 (1987), incorporated herein by reference. The reverse transcriptase reaction was conducted according to the protocol of the manufacturer (Promega, Wis.) using 10 μg of RNA.

The reaction mixture was extracted with phenolchloroform, precipitated with ethanol and resuspended in Taq polymerase buffer. The subsequent PCR was performed over 35 cycles of amplification following an initial denaturation at 94° C. for 5 minutes, annealing at 55° C. for 30 seconds and extension at 72° C. for 5 minutes. The Taq Polymerase was added to the reaction mixture after denaturation only. The subsequent PCR settings were: denaturation at 94° C. for 45 seconds, annealing at 55° C. for 1 minute and extension at 72° C. for 4 minutes. The primers used for this reaction were MKNHE (SEQ ID NO: 1) and sequencing primer UP6: TCGGCCGCCTGAAGGAGC (SEQ ID NO: 3) (see FIG. 2).

The sequencing strategy as well as a restriction map and the genomic structure of the b.IAP gene are shown in FIG. 2. The strategies for subcloning the coding region of the gene into an expression vector using PCR and for construction of a full length cDNA by means of RT-PCR are indicated in FIG. 2. A single fragment of approximately 830 bp been obtained from RT-PCR as could be expected from the genomic sequence.

EXAMPLE VIII

Characterization of Recombinant Calf IAP

The sequence for the calf intestinal AP gene was determined as described above. A full length CDNA was constructed using a partial cDNA clone (BB204) and a fragment obtained by RT-PCR.

A CDNA fragment clone (R201) and a corresponding genomic clone were obtained, which resemble properties of a putative pseudogene. Both clones contain STOP codons within the coding region and several frameshifts. Bands corresponding to the putative pseudogene could only be identified upon hybridizing with a mouse TNAP CDNA which gave a distinct pattern. This result suggests that the bands corr espond to TSAP genes only, and that the pseudogene is more related to TNAP. In contrast, the murine pseudogene has been found to resemble more homology to the mouse EAP gene (Manes et al., supra).

The sequence and genomic structure of the b.IAP gene show high homology to all known TSAP genes. The smallest exon, exon VII, is only 73 bp long while the longest exon, exon XI, is approximately 1.1 kb long. The exact length of exon 11 cannot be determined since no cDNA with a poly-A tail had been isolated. The estimate given is based on the identification of a putative polyadenylation site AATAAA (bp 5183–5188) in the 3' non-coding region of the gene (underlined in FIG. 1). The introns are among the smallest introns reported (Hawkins,, Nucl. Acids Res. 16:9893–9908 (1988)) as was found in the case of other TSAP genes as well (Manes et al., supra; Hernthorn et al., supra; Knoll et al., supra; Millan and Manes, sur). The largest one, splitting exon V and exon VI, is only 257 bp long. All exon-intron junctions conform to the GT-AG rule (Breathnach et al., Proc. Natl. Acad, Sci, USA 75:4853–4857 (1978)) and also onform well to the consensus sequences (C/A)AG/GT(A/G)AGT (SEQ ID NO: 4) and $(T/C)_nN(C/T)AG/G$ (SEQ ID NO: 5) for donor and acceptor sites, respectively (Mount, Nucl. Acids Res. 10:459–473 (1982)).

Interestingly, the entire coding region of exon XI shows a high G/C content of over 60 to 80% compared to a rather equal ratio of G/C to A/T throughout the whole structural gene. Other regions of biased GC content were found at bp 270 to bp 490 with a high A/T content and in a region preceding the poly adenylation site, which again shows a high G/C content.

A putative TATA-box has been identified in the 1.5 kb of sequence preceding the coding region (bp 1395–1400, underlined in FIG. 1). It shows the same variant ATTTAA sequence embedded in a conserved region of 25 bp as was previously reported for the mouse TSAP genes (Manes et al., supra) and two human TSAP genes (Millan, Nucl. Acids Res. 15:10599 (1987); Millan and Manes, supra)).

The sequence GGGAGGG has been shown to be part of the putative mouse TSAP promoters (Manes et al., supra) as well as of two human TSAP promoters (Millan, (1987), supra; Millan and Manes, suDra). This sequence is also present in the putative promoter region of the b.IAP gene.

The sequence CACCC or its complementary reverse is repeated 6 times in the region of bp 1182–1341, 24 times in the entire structural gene and 31 times throughout the whole sequence shown here. However, only one less conserved CACCC box (Myers et al., Science 232:613–618 (1986)) was identified.

Since it was shown for dog IAP that the enzyme can be induced by cortico steroid hormone (Sanecki et al., Am. J. Vet. Res. 51, 12:1964–1968 (1990)), hormone responsive elements in the genomic sequence of b.IAP were identified. Palindromic and direct repeats, known to be binding sites for dimeric nuclear factors as described in O'Malley, Mol. Endocrinol. 5:94–99 (1990), were identified in the 1.5 kb upstream of the initiation codon. A long, imperfect palindromic repeat $(CACACCTCCTGCCCAG-N_7-CTGGTGAGGAGCTGAG)$ (SEQ ID NO: 6) extends from bp 899 to bp 937. A direct repeat of the sequence GGGCAGG spaced by three nucleotides starts at bp 1311.

Several regions of high homology to mouse (Manes et al., supra) and human (Millan, (1987), supra) IAP genes have been identified in the putative promoter region. However, one stretch of 10 bp (AGCCACACCC) (SEQ ID NO: 7) was found to be identical with a sequence in the same region upstream of the TATA box of the human β-globin gene (Myers et al., supra).

Another region of interest precedes the putative poly adenylation site at bp 5016. The sequence ACAGAGAG-GAGA (SEQ ID NO: 8) is imperfectly repeated, spaced by an inverted repeat overlapping the last adenine nucleotide (ACAG-T-GACA). The presented 1.5 kb of the presumed promoter of the b.IAP gene contain several additional putative regulatory elements. A short stretch of 14 alternating thymines and guanines, intercepted by one adenine was found at position 601 of the sequence. Interestingly, this sequence is identical to a part of a slightly longer stretch with the same characteristics beginning at bp 2713 within the intron splitting exon V and VI. Another stretch of 36 alternating pyridines and purines is found at position 732 being mainly composed of cytosin and adenine nucleotides. Identical structures are reported for the human germ cell AP gene (Millan and Manes, supra) and are thought to form Z-DNA structures, which may play a role in the regulation of gene expression (Nordheim and Rich, Nature (London) 303:674–678 (1983).

As shown in FIG. 3, the deduced amino acid sequence of b.IAP is highly homologous to all known IAPs. Identical residues and conservative amino acid substitutions are found within structurally important regions, as is the case for the other TSAPs as well, hereas variability is almost exclusively found at the C-erminus and in the highly variable loops (Millan, (1988), supra).

$Asp^{487}$ of b.IAP resides within a conserved sequence of 4 amino acids in the same region of the human intestinal gene (indicated in FIG. 3) as well as of human PLAP (Millan, J. Biol. Chem, 261:3112–3115 (1986)). This residue was shown for PLAP to be the attachment site of a phosphatidyl-inositol membrane anchor (Micanovic et al., Proc. Natl. Acad. Sci. USA 87:157–161 (1990)). Evidence has been presented previously that b.IAP is also anchored to the plasma membrane in such a fashion. There appears to be a spatial regulated release of IAP into the lumen without cleavage of the anchor in a variety of species (Hoffmann-Blume et al., Eur. J. Biochem. 199:305–312 (1991)).

EXAMPLE IX

Comparison of Purified and Recombinant Forms of Calf IAP

Values for $K_m$ and $K_i$ for L-Phe were determined for the recombinant enzyme as well as for purified protein from calf intestine as described in Hummer and Millan, supra, and Wilkinson, *Biochem. J.* 8:324–332 (1961), incorporated herein by reference. Both the purified b.IAP from natural sources and the recombinant b.IAP show identical values for $K_m$ (within standard deviations), and only slightly different values of $K_I$. $K_m$ was determined as 0.77=0.12 for the recombinant enzyme and as 0.86±0.17 for the purified natural enzyme. $K_1$ for L-Phe were found to be 15.2±1.8 and 11.2±1.0 for the recombinant and purified enzymes, respectively. Thus, the results of these findings indicate that the natural and recombinant forms of calf IAP have comparable properties and activities.

Two possible glycosylation sites appear to be conserved between the human and the bovine IAP. Three other possible sites within other IAP sequences were not found in the b.IAP. The high degree of heterologous glycosylation of the purified enzyme was demonstrated by isoelectric focusing (IEF). IEF was performed using the Resolve-ALP system (Isolab, Akron, OH) as described in Griffiths & Black, *Clinn. Chem.* 33:2171–2177 (1987). Samples of recombinant and purified enzyme were run either treated with neuraminidase or untreated to compare the amount of glycosylation.

A smeary band was obtained upon IEF of untreated purified enzyme in contrast to a more distinct band for the recombinant b.IAP protein. After treatment with neuraminidase, both bands dissolve into several sharp bands, in which the purified enzyme showed considerably more diversity than the recombinant enzyme.

EXAMPLE X

Heat Inactivation of Calf IAP

Figure 4:
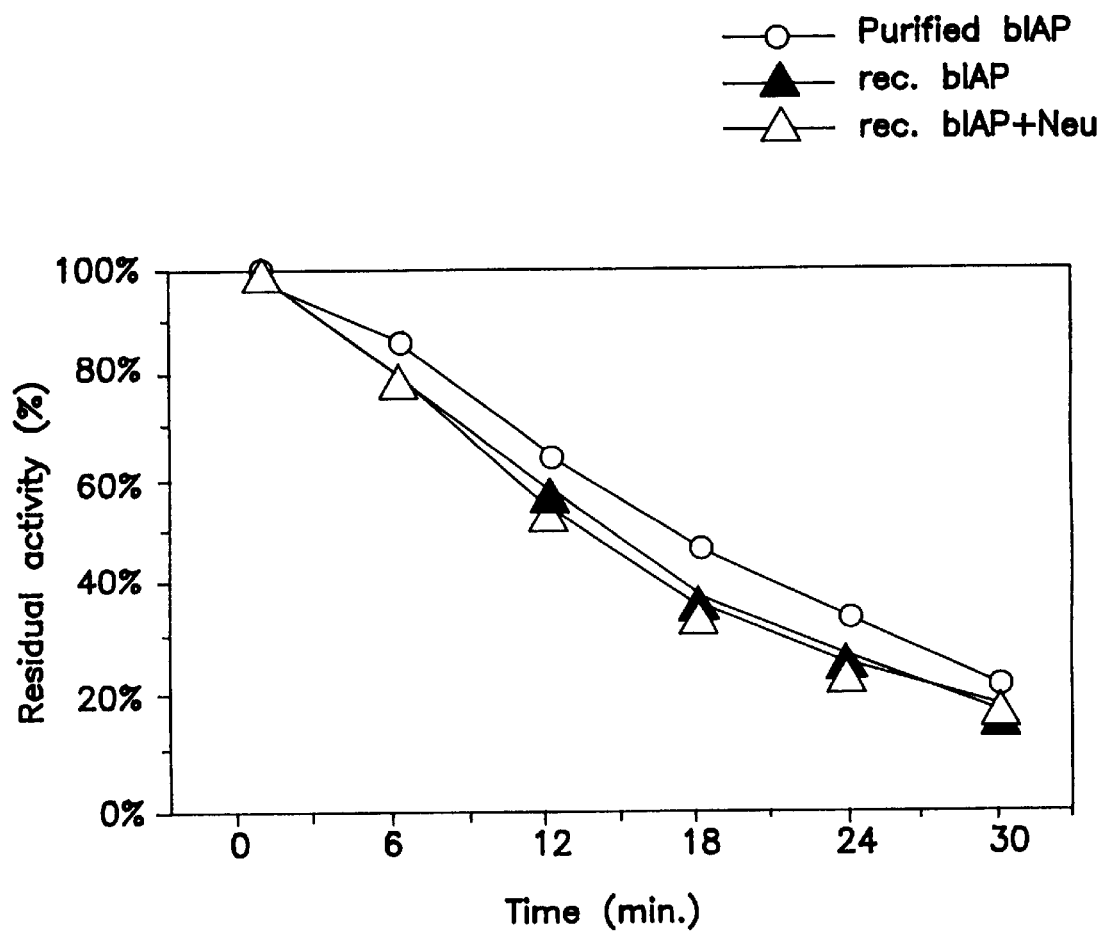
FIG. 4 shows the results of studies relating to the heat inactivation of purified and recombinant calf IAP.

The heat stabilities of purified calf IAP and recombinant calf IAP were determined at 56° C. First, the enzyme samples were diluted in 1 ml of DEA buffer containing 1M DEA diethanolamine (pH 9.8) containing 0.5 mM $MgCl_2$ and 20 μM $ZnCl_2$. The solution was heated at 56° C. for the fixed time intervals indicated in Table I. Fifty μl of the enzyme solution were removed and pipetted into a microtiter well and stored on ice until the end of the longest incubation period. At the end of the experiment, the residual activity was.measured by the addition of 200 μl of DEA buffer containing p-nitrophenylphosphate (10 mM) in DEA buffer. For comparison, a sample of recombinant enzyme was pretreated with 0.2 units/ml of neuriminidase for 16 hours at room temperature, followed by the same heat inactivation treatment. The results of the heat. inactivation studies are shown in FIG. 4.

TABLE I

Heat Inactivation of Intestinal AP

| | Time (minutes) | | | | | |
|---|---|---|---|---|---|---|
| | 0' | 6' | 12' | 18' | 24' | 30' |
| | | | Residual activity (%) | | | |
| Calf IAP (intestinal extract) | 100 | 87 | 65.6 | 48.7 | 36 | 23.4 |
| Recombinant IAP | 100 | 80.6 | 59.5 | 39.6 | 28.5 | 18.5 |
| Recombinant IAP upon Neuriminidase | 100 | 80.8 | 55.9 | 38.1 | 27.1 | 20.3 |

The foregoing description of the invention is exemplary for purposes of illustration and explanation. It should be understood that various modifications can be made without departing from the spirit and scope of the invention. Accordingly, the following claims are intended to be interpreted to embrace all such modifications.

I claim:

1. A recombinant calf intestinal alkaline phosphatase (cIAP) polypeptide.

2. The recombinant cIAP of claim 1, comprising the amino acid sequence shown in FIG. 1 (SEQ ID NO: 10).

3. A recombinant calf intestinal alkaline phosphatase (cIAP) polypeptide produced by a host cell from a vector comprising a nucleotide sequence encoding cIAP.

4. The recombinant cIAP of claim 3, wherein said nucleotide sequence is SEQ.ID NO: 9.

5. The recombinant cIAP of claim 3, wherein said nucleotide sequence encodes SEQ ID NO: 10.

6. A composition of matter, comprising a recombinant calf intestinal alkaline phosphatase attached to a reagent having specific reactivity with a desired ligand.

7. The composition of matter of claim 6, wherein said reagent is an antibody.

8. A method for identifying the presence of a ligand in a sample, comprising the steps of:
   a) contacting the sample with a recombinant calf intestinal alkaline phosphatase (cIAP), wherein said recombinant cIAP is attached to a reagent that specifically binds the ligand;
   b) contacting the sample with a substrate for the recombinant cIAP, wherein catalysis of the substrate by cIAP provides a detectable signal; and
   c) detecting the presence of the detectable signal, said signal indicating that the reagent bound to the sample, thereby identifying the presence of the ligand in the sample.

9. The method of claim 8, further comprising the step of d) determining an amount of binding of said sample to the reagent, wherein the amount of binding relates to the concentration of said ligand in the sample.

10. The method of claim 8, wherein said reagent is an anti-ligand and antibody.

11. The method of claim 8, wherein said reagent is an oligonucleotide.

12. The method of claim 11, wherein said ligand is a cDNA or genomic DNA fragment.

* * * * *

UNITED STATES PATENT AND TRADEMARK OFFICE
CERTIFICATE OF CORRECTION

PATENT NO. : 5,773,226
DATED : Jun. 30, 1998
INVENTOR(S) : Jose L. Millan

It is certified that error appears in the above-indentified patent and that said Letters Patent is hereby corrected as shown below:

Column 1, line 59, please delete "15".

Column 3, line 8, please delete "More." and replace therefor with --More--.

Column 5, line 37, please delete "etermine" and replace therefor with --determine--.

Column 5, line 51, please delete "CDNA" and replace therefor with --cDNA--.

Column 6, line 15, please delete "CDNA" and replace therefor with --cDNA--.

Column 6, line 17, please delete "CDNA" and replace therefor with --cDNA--.

Column 6, line 19, please delete "CDNA" and replace therefor with --cDNA--.

Column 6, line 20, please delete "CDNA" and replace therefor with --cDNA--.

UNITED STATES PATENT AND TRADEMARK OFFICE
CERTIFICATE OF CORRECTION

PATENT NO. : 5,773,226
DATED : Jun. 30, 1998
INVENTOR(S) : Jose L. Millan

It is certified that error appears in the above-indentified patent and that said Letters Patent is hereby corrected as shown below:

Column 6, line 31, please delete "CDNA" and replace therefor with --cDNA--.

Column 6, line 41, please delete "CDNA" and replace therefor with --cDNA--.

Column 7, line 16, please delete "CDNA" and replace therefor with --cDNA--.

Column 7, line 37, please delete "RcDNA" and repplace therefor with --pc DNA--

Column 7, line 62, please delete "Fragmnent" and replace therefor with --Fragment--.

Column 8, line 5, please delete "pe DNA" and replace therefor with --pc DNA--.

Column 8, line 5, please delete "expressiqon" and replace therefor with --expression--.

UNITED STATES PATENT AND TRADEMARK OFFICE
CERTIFICATE OF CORRECTION

PATENT NO. : 5,773,226
DATED : Jun. 30, 1998
INVENTOR(S) : Jose L. Millan

It is certified that error appears in the above-indentified patent and that said Letters Patent is hereby corrected as shown below:

Column 8, line 21, please delete "gran," and replace therefor with --supra,--

Column 8, line 50, please delete "NA" and replace therefor with --RNA--.

Column 9, line 9, please delete "bp been" and replace therefor with --bp had been--

Column 9, line 16, please delete "CDNA" and replace therefor with --cDNA--.

Column 9, line 19, please delete "CDNA" and replace therefor with --cDNA--.

Column 9, line 24, please delete "CDNA" and replace therefor with --cDNA--.

Column 9, line 42, please delete "sur)" and replace therefor with --supra)--.

Column 9, line 46, please delete "onform" and replace therefor with --conform--.

UNITED STATES PATENT AND TRADEMARK OFFICE
CERTIFICATE OF CORRECTION

PATENT NO. : 5,773,226
DATED : June 30, 1998
INVENTOR(S) : Jose L. Millan

It is certified that error appears in the above-identified patent and that said Letters Patent is hereby corrected as shown below:

Column 10, line 1, please delete "suDra)" and replace therefor with --supra)--.

Column 10, line 48, please delete "hereas" and replace therefor with --whereas--.

Column 10, line 49, please delete "C-erminus" and replace therefor with --C-terminus--.

Column 12, line 8, please delete "was.measured" and replace therefor with --was measured--.

UNITED STATES PATENT AND TRADEMARK OFFICE
CERTIFICATE OF CORRECTION

PATENT NO. : 5,773,226
DATED : Jun. 30, 1998
INVENTOR(S) : Jose L. Millan

It is certified that error appears in the above-identified patent and that said Letters Patent is hereby corrected as shown below:

Column 12, line 13, please delete "heat. inactivation" and replace therefor with --heat inactivation--.

Column 33, line 53, claim 4, please delete "cIAP.of" and replace therefor with --cIAP of--.

Column 34, line 59, claim 10, please delete "anti-ligand and antibody" and replace therefor with --anti-ligand antibody--.

Column 34, line 62, claim 12, please delete "claim 11" and replace therefor with --claim 8--.

Signed and Sealed this

Second Day of March, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:1:

Met  Lys  Asn  His  Glu
    1                            5

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCTAGCCATG CAGGGGCCT GCG                        2 3

( 2 ) INFORMATION FOR SEQ ID NO:3:

( i ) SEQUENCE CHARACTERISTICS:
     ( A ) LENGTH: 18 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:3:

TCGGCCGCCT GAAGGAGC                                                    18

( 2 ) INFORMATION FOR SEQ ID NO:4:

( i ) SEQUENCE CHARACTERISTICS:
          ( A ) LENGTH: 6 base pairs
          ( B ) TYPE: nucleic acid
          ( C ) STRANDEDNESS: single
          ( D ) TOPOLOGY: linear ( i x ) FEATURE:
          ( A ) NAME/KEY: misc_feature
          ( B ) LOCATION: complement (1)
          ( D ) OTHER INFORMATION: /note= "N=C OR A"

( i x ) FEATURE:
          ( A ) NAME/KEY: misc_feature
          ( B ) LOCATION: complement (2)
          ( D ) OTHER INFORMATION: /note= "N=AG OR GT"

( i x ) FEATURE:
          ( A ) NAME/KEY: misc_feature
          ( B ) LOCATION: complement (3)
          ( D ) OTHER INFORMATION: /note= "N=A OR G"

( x i ) SEQUENCE DESCRIPTION: SEQ ID NO:4:

NNNAGT                                                                  6

( 2 ) INFORMATION FOR SEQ ID NO:5:

( i ) SEQUENCE CHARACTERISTICS:
          ( A ) LENGTH: 4 base pairs
          ( B ) TYPE: nucleic acid
          ( C ) STRANDEDNESS: single
          ( D ) TOPOLOGY: linear ( i x ) FEATURE:
          ( A ) NAME/KEY: misc_feature
          ( B ) LOCATION: complement (1)
          ( D ) OTHER INFORMATION: /note= "Y=T OR C"

( i x ) FEATURE:
          ( A ) NAME/KEY: misc_feature
          ( B ) LOCATION: complement (3)
          ( D ) OTHER INFORMATION: /note= "Y=C OR T"

( i x ) FEATURE:
          ( A ) NAME/KEY: misc_feature
          ( B ) LOCATION: complement (4)
          ( D ) OTHER INFORMATION: /note= "Y=AG OR G"

( x i ) SEQUENCE DESCRIPTION: SEQ ID NO:5:

YNYY                                                                    4

( 2 ) INFORMATION FOR SEQ ID NO:6:

( i ) SEQUENCE CHARACTERISTICS:
          ( A ) LENGTH: 39 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:6:

CACACCTCCT GCCCAGNNNN NNNCTGGTGA GGAGCTGAG                              39

( 2 ) INFORMATION FOR SEQ ID NO:7:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

AGCCACACCC                                                                                      10

( 2 ) INFORMATION FOR SEQ ID NO:8:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

ACAGAGAGGA GA                                                                                   12

( 2 ) INFORMATION FOR SEQ ID NO:9:

( i ) SEQUENCE CHARACTERISTICS:
    ( A ) LENGTH: 5399 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: join(1501..1567, 1647..1763, 1878..1993, 2179
          . . 2353, 2433..2605, 2864..2998, 3084..3156, 3257
          . . 3391, 3475..3666, 3879..3995, 4101..4402)

( x i ) SEQUENCE DESCRIPTION: SEQ ID NO:9:

| | | | | | | |
|---|---|---|---|---|---|---|
| AAGCTTTCAC | CTTCTCTGAA | AACAGAGAGA | CAGTCCTCAG | CCCCAGTCCT | CACCCTTCCT | 60 |
| ACCTCCCTGC | CTGATGCCCA | GGCAATCATC | TGGTGGCGTG | TCACCTCCCT | CTGTCCCATG | 120 |
| AGTTCCACTA | GATGTGGCCC | TCAAGAAAAA | GGGCTTCCCT | GTTGGCTCAG | CTGGTAAAGA | 180 |
| ATCCTCCAGC | AATGTAGGAG | ACCTGGGTTC | GATCCCTGGG | TTGGGAGGAT | ACCCTGGAGA | 240 |
| AGGGAATGGC | TACCCACTCC | AGTATTCTTG | CCTGGATAAT | CCCATGGACA | GAGGAGTCTG | 300 |
| GCAGGCTGCA | GACCATAAGG | TAGAAAGAGT | CAGACATGAC | TGAGCAACTA | AGCACAATAT | 360 |
| TCCACTGGAT | ATATCATACT | TTGTTCATCC | ATTTGTCTGC | TGTGGATGGT | TGAGTGGCTT | 420 |
| GTGCCTCTTG | GCTACTGTGA | GTAATGCTAC | TAAAATGTGA | GTGTGCAAAT | ACCTCTTATA | 480 |
| GATCTTGATT | TCAATTATTG | GGGATACACA | CCCAGAAGGC | GGATTGTTGG | ATGTGAGAAT | 540 |
| GCCTTTTTGA | ACCCCAACCT | GGGGTTACTG | AAACCCTAGC | TCCTTATCAG | AAGCTGTTCC | 600 |
| TGTGAGTGTG | TGTGGCCTGT | GGAGAGAAGA | GACTCACCTC | TGCCTTCCAT | TTACCTCTCC | 660 |
| AATGGAGCAG | AGGTTGCAAA | CTTCAGTTAA | TGGGCACTGG | GCCCACGCCT | GTCGACCCGT | 720 |
| TACAGGCACC | TTACACACAC | ACACACACAC | ACACACACAC | ACAAACAGCA | CTGCAGACCC | 780 |
| AGCTCTTCAG | TAACTGAAGA | CACAGACAAG | GCCCCCGCTC | TGCTGTCACC | TCCAGTCCCA | 840 |
| TCCTTCTCCA | CAGCAGAAGC | TGGGCCCAGG | CTCCCATGTG | CCCCACTAG | CCCAGTGCCC | 900 |
| ACACCTCCTG | CCCAGGTCAA | GTCTGGTGAG | GAGCTGAGCA | GGGGGCAGGG | CAGACAGGCC | 960 |
| TCCCCGTGGA | TCTCTGTCTC | AGGGCGCCAG | GGAACTAACC | CAGGCCCTG | GCCAGGCTGT | 1020 |
| GTCCCTAAGC | ACTGGGAACC | AAACCAGGCC | AAGGCTGAGT | CTCAGAAAAC | ACTGAACACG | 1080 |

| | | | | | |
|---|---|---|---|---|---|
| TGAAGGAAGG | AGAGATGGTT | CTCCCACAGG | ACTTGGTGAG | CAGAGGGCTG | GGAGGAGCCT | 1140 |
| CAGTCAGGAC | CTTGAAAACG | TTCCTCAGGC | CTAGACATCT | GCACCCTAAT | CCCCACCCCA | 1200 |
| CCCTGAGGAG | ACAGCTGGGA | CCATCCTGGG | AGGGAGGGAC | CTGAATCCTC | AGGACCCCTA | 1260 |
| CTGCTAAGCC | ACACCCACCA | CATGCCCCTG | GCAACAGGGC | TCAAAGTCAT | AGGGCAGGTG | 1320 |
| AGGGGCAGGG | TGTGGCCACC | CGGGGAACCT | GGGATGGACA | AGGAGACTTT | AATAGCAGGG | 1380 |
| ACAAAGTCTA | TCTAGATTTA | AGCCCAGCAG | GCCAAGCTGC | AGCCGGTCCC | TGGTGTCCCA | 1440 |
| GCCTTGCCCT | GAGACCCGGC | CTCCCAGGT  | CCCATCCTGA | CCCTCTGCCA | TCACACAGCC | 1500 |

```
ATG CAG GGG GCC TGC GTG CTG CTG CTG CTG GGC CTG CAT CTA CAG CTC        1548
Met Gln Gly Ala Cys Val Leu Leu Leu Leu Gly Leu His Leu Gln Leu
 1               5                  10                  15

TCC CTA GGC CTC GTC CCA  G GTAATCAGGC GGCTCCAGC AGCCCCTACT             1597
Ser Leu Gly Leu Val Pro
                 20

CACAGGGGCG GCTCTAGGCT GACCTGACCA ACACTCTCCC CTTGGGCAG  TT GAG          1651
                                                         Val Glu
GAG GAA GAC CCC GCC TTC TGG AAC CGC CAG GCA GCC CAG GCC CTC GAT        1699
Glu Glu Asp Pro Ala Phe Trp Asn Arg Gln Ala Ala Gln Ala Leu Asp
 25                  30                  35                  40

GTG GCT AAG AAG CTG CAG CCC ATC CAG ACA GCC GCC AAG AAT GTC ATC        1747
Val Ala Lys Lys Leu Gln Pro Ile Gln Thr Ala Ala Lys Asn Val Ile
         45                  50                  55

CTC TTC TTG GGG GAT  G GTGAGTACAT GAGGCCAGCC CACCCCCTGT                1793
Leu Phe Leu Gly Asp
                 60

CCCCTGACAG GCCTGGAACC CTGTGATGCC GGCTGACCCA GGTTGGCCCC AGAAACTCGG      1853
ACCTGAGACA CTGTGTACCT TCAG  GG ATG GGG GTG CCT ACG GTG ACA GCC         1903
                            Gly Met Gly Val Pro Thr Val Thr Ala
                                     65                  70

ACT CGG ATC CTA AAG GGG CAG ATG AAT GGC AAA CTG GGA CCT GAG ACA        1951
Thr Arg Ile Leu Lys Gly Gln Met Asn Gly Lys Leu Gly Pro Glu Thr
             75                  80                  85

CCC CTG GCC ATG GAC CAG TTC CCA TAC GTG GCT CTG TCC AAG                1993
Pro Leu Ala Met Asp Gln Phe Pro Tyr Val Ala Leu Ser Lys
         90                  95                  100

GTAAGGCCAA GTGGCCTCAG GGTGGTCTAC ACCAGAGGGG TGGGTGTGGG CCTAGGGAGC      2053
AGGGTAGGAG GGAAACCCAG GAGGGCTAGG GGCTGAGATA GGGGCTGGGG GCTGTGAGGA      2113
TGGGCCCAGG GCTGGGTCAG GAGCTGGGTG TCTACCCAGC AGAGCGTAAG GCATCTCTGT      2173
CCCAG ACA TAC AAC GTG GAC AGA CAG GTG CCA GAC AGC GCA GGC ACT          2220
      Thr Tyr Asn Val Asp Arg Gln Val Pro Asp Ser Ala Gly Thr
                     105                 110

GCC ACT GCC TAC CTG TGT GGG GTC AAG GGC AAC TAC AGA ACC ATT GGT        2268
Ala Thr Ala Tyr Leu Cys Gly Val Lys Gly Asn Tyr Arg Thr Ile Gly
115                  120                 125                 130

GTA AGT GCA GCC GCC CGC TAC AAC CAG TGC AAA ACG ACA CGT GGG AAT        2316
Val Ser Ala Ala Ala Arg Tyr Asn Gln Cys Lys Thr Thr Arg Gly Asn
             135                 140                 145

GAG GTC ACG TCT GTG ATG AAC CGG GCC AAG AAA GCA  G GTGGGCTTGG          2363
Glu Val Thr Ser Val Met Asn Arg Ala Lys Lys Ala
150                  155

GCGTCAGCTT CCTGGGCAGG GACGGGCTCA GAGACCTCAG TGGCCCACCG TGACCTCTGC      2423
CACCCTCAG  GG AAG TCC GTG GGA GTG GTG ACC ACC ACC AGG GTG CAG          2470
           Gly Lys Ser Val Gly Val Val Thr Thr Thr Arg Val Gln
                          160                 165                 170

CAT GCC TCC CCA GCC GGG GCC TAC GCG CAC ACG GTG AAC CGA AAC TGG        2518
```

```
                His  Ala  Ser  Pro  Ala  Gly  Ala  Tyr  Ala  His  Thr  Val  Asn  Arg  Asn  Trp
                               175                      180                     185

TAC  TCA  GAC  GCC  GAC  CTG  CCT  GCT  GAT  GCA  CAG  ATG  AAT  GGC  TGC  CAG                    2566
Tyr  Ser  Asp  Ala  Asp  Leu  Pro  Ala  Asp  Ala  Gln  Met  Asn  Gly  Cys  Gln
               190                      195                     200

GAC  ATC  GCC  GCA  CAG  CTG  GTC  AAC  AAC  ATG  GAT  ATT  GAC  GTGCGACATG                       2615
Asp  Ile  Ala  Ala  Gln  Leu  Val  Asn  Asn  Met  Asp  Ile  Asp
               205                      210                     215

TTGGGCACAG GGCGGGGCTG GGCACAGGTG GTGGGGCACA CTCGCAACAC AGTCGTAGGT                                  2675

AACCTCCAGC CTGCGGTGTT TCAGGGTTTT CATGGGTTTG TGTGTGTGTG TATGTGTGGT                                  2735

GGGGTGGCAC CATGTAGGAG GTGGGGACAG GCCTTTCCCA CAGACCTGGT GGGGGAGGTA                                  2795

GGGGCTGTGT GAGAGGAGTA AAGGGCCAGC CAGGCCCCTA ACCCACCTGC CTAACTCTCT                                  2855

GGCTCCAG GTG ATC CTG GGT GGA GGC CGA AAA TAC ATG TTT CCT GTG GGG                                  2905
         Val  Ile  Leu  Gly  Gly  Gly  Arg  Lys  Tyr  Met  Phe  Pro  Val  Gly
                   220                      225                          230

ACC  CCA  GAC  CCT  GAA  TAC  CCA  GAT  GAT  GCC  AGT  GTG  AAT  GGA  GTC  CGG                    2953
Thr  Pro  Asp  Pro  Glu  Tyr  Pro  Asp  Asp  Ala  Ser  Val  Asn  Gly  Val  Arg
               235                      240                     245

AAG  CGA  AAG  CAG  AAC  CTG  GTG  CAG  GCA  TGG  CAG  GCC  AAG  CAC  CAG                         2998
Lys  Arg  Lys  Gln  Asn  Leu  Val  Gln  Ala  Trp  Gln  Ala  Lys  His  Gln
               250                      255                     260

GTAATGGGGG CTCACGGATG TGGGGGTACA GTGGGCTGG GCCTGGGGTG TCGGCTATGG                                   3058

CTGAGGCCTG GTTCTGCCCT CCCAG GGA GCC CAG TAT GTG TGG AAC CGC ACT                                   3110
                            Gly  Ala  Gln  Tyr  Val  Trp  Asn  Arg  Thr
                                          265                      270

GCG  CTC  CTT  CAG  GCG  GCC  GAT  GAC  TCC  AGT  GTA  ACA  CAC  CTC  ATG    G                    3156
Ala  Leu  Leu  Gln  Ala  Ala  Asp  Asp  Ser  Ser  Val  Thr  His  Leu  Met
               275                      280                     285

GTAACGACTC CACCCACCCT CACTGTCCTC CCCAGGAATG GGTGCCATGG GCCACCCCTG                                  3216

TCCTCAGCTT GAGGGTCACC ACTGCTCCCC TTTCCCACAG  GC CTC TTT GAG CCG                                   3270
                                              Gly Leu  Phe  Glu  Pro
                                                              290

GCA  GAC  ATG  AAG  TAT  AAT  GTT  CAG  CAA  GAC  CAC  ACC  AAG  GAC  CCG  ACC                    3318
Ala  Asp  Met  Lys  Tyr  Asn  Val  Gln  Gln  Asp  His  Thr  Lys  Asp  Pro  Thr
               295                      300                     305

CTG  CAG  GAA  ATG  ACA  GAG  GTG  GCC  CTG  CGA  GTC  GTA  AGC  AGG  AAC  CCC                    3366
Leu  Gln  Glu  Met  Thr  Glu  Val  Ala  Leu  Arg  Val  Val  Ser  Arg  Asn  Pro
               310                      315                     320

AGG  GGC  TTC  TAC  CTC  TTT  GTG  GAG   G GTGAGTGGCA GCCCCTTGGT                                   3411
Arg  Gly  Phe  Tyr  Leu  Phe  Val  Glu
               325                      330

GAACAGAGGT GTGATGAGGG CCATCAGGGT GGGTTTGGTA TCTTATATGT GACTTATCTG                                  3471

CAG  GA GGC CGC ATT GAC CAC GGT CAC CAT GAT GAC AAA GCT TAT ATG                                    3518
        Gly Gly Arg Ile Asp His Gly His His Asp Asp Lys Ala Tyr Met
                         335                  340                 345

GCA  CTG  ACC  GAG  GCG  GGT  ATG  TTT  GAC  AAT  GCC  ATC  GCC  AAG  GCT  AAT                    3566
Ala  Leu  Thr  Glu  Ala  Gly  Met  Phe  Asp  Asn  Ala  Ile  Ala  Lys  Ala  Asn
                    350                     355                     360

GAG  CTC  ACT  AGC  GAA  CTG  GAC  ACG  CTG  ATC  CTT  GTC  ACT  GCA  GAC  CAC                    3614
Glu  Leu  Thr  Ser  Glu  Leu  Asp  Thr  Leu  Ile  Leu  Val  Thr  Ala  Asp  His
                    365                     370                     375

TCT  CAT  GTC  TTC  TCT  TTT  GGT  GGC  TAT  ACA  CTG  CGT  GGG  ACC  TCC  ATT                    3662
Ser  His  Val  Phe  Ser  Phe  Gly  Gly  Tyr  Thr  Leu  Arg  Gly  Thr  Ser  Ile
                    380                     385                     390

TTT    G GTAAGCCCAG GGAGAGTGGC AGGTCGTTGC CCTAAGTTA CGAGGCACAA                                     3716
Phe
```

```
CTCGTCTGAG CCAGTTCCTC TATCTGTCTA GTGGGGTAGT ACAGCACACT GCCTGCTACG       3776

CTCTGGTGAG GATTGTCACT GACAGACAGA CTGGCCATGG CTCTGCACAC AGGGGAGCAC       3836

AAGCTAGGTC AGTGTGATCA CGGGGTCCCC TCTTCCCTGA AG  GT CTG GCC CCC         3889
                                                    Gly Leu Ala Pro
                                                    395
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| AGC | AAG | GCC | TTA | GAC | AGC | AAG | TCC | TAC | ACC | TCC | ATC | CTC | TAT | GGC | AAT | 3937 |
| Ser | Lys | Ala | Leu | Asp | Ser | Lys | Ser | Tyr | Thr | Ser | Ile | Leu | Tyr | Gly | Asn |      |
| 400 |     |     |     |     | 405 |     |     |     |     | 410 |     |     |     |     |     |      |
| GGC | CCA | GGC | TAT | GCG | CTT | GGC | GGG | GGC | TCG | AGG | CCC | GAT | GTT | AAT | GAC | 3985 |
| Gly | Pro | Gly | Tyr | Ala | Leu | Gly | Gly | Gly | Ser | Arg | Pro | Asp | Val | Asn | Asp |      |
| 415 |     |     |     |     | 420 |     |     |     |     | 425 |     |     |     |     | 430 |      |

```
AGC ACA AGC  G GTAAGTGTAG TAGGTGGGGC GCTGGGAGGT GGGGACCCTG              4035
Ser Thr Ser
GCCAGAAATT GTGGGGAGGG GAAGGCTGCC TCCCTTGTCA CATTAACTTC CCTTCTTCTG       4095

GCCAG  AG GAC CCC TCG TAC CAG CAG CAG GCG GCC GTG CCC CAG GCT          4141
       Glu Asp Pro Ser Tyr Gln Gln Gln Ala Ala Val Pro Gln Ala
           435                 440                 445
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| AGC | GAG | ACC | CAC | GGG | GGC | GAG | GAC | GTG | GCG | GTG | TTC | GCG | CGC | GGC | CCG | 4189 |
| Ser | Glu | Thr | His | Gly | Gly | Glu | Asp | Val | Ala | Val | Phe | Ala | Arg | Gly | Pro |      |
|     | 450 |     |     |     |     | 455 |     |     |     |     | 460 |     |     |     |     |      |
| CAG | GCG | CAC | CTG | GTG | CAC | GGC | GTC | GAG | GAG | GAG | ACC | TTC | GTG | GCG | CAC | 4237 |
| Gln | Ala | His | Leu | Val | His | Gly | Val | Glu | Glu | Glu | Thr | Phe | Val | Ala | His |      |
| 465 |     |     |     |     | 470 |     |     |     |     | 475 |     |     |     |     |     |      |
| ATC | ATG | GCC | TTT | GCG | GGC | TGC | GTG | GAG | CCC | TAC | ACC | GAC | TGC | AAT | CTG | 4285 |
| Ile | Met | Ala | Phe | Ala | Gly | Cys | Val | Glu | Pro | Tyr | Thr | Asp | Cys | Asn | Leu |      |
| 480 |     |     |     |     | 485 |     |     |     |     | 490 |     |     |     |     | 495 |      |
| CCA | GCC | CCC | ACC | ACC | GCC | ACC | AGC | ATC | CCC | GAC | GCC | GCG | CAC | CTG | GCG | 4333 |
| Pro | Ala | Pro | Thr | Thr | Ala | Thr | Ser | Ile | Pro | Asp | Ala | Ala | His | Leu | Ala |      |
|     |     |     |     | 500 |     |     |     |     | 505 |     |     |     |     | 510 |     |      |
| GCC | AGC | CCG | CCT | CCA | CTG | GCG | CTG | CTG | GCT | GGG | GCG | ATG | CTG | CTG | CTG | 4381 |
| Ala | Ser | Pro | Pro | Pro | Leu | Ala | Leu | Leu | Ala | Gly | Ala | Met | Leu | Leu | Leu |      |
|     |     | 515 |     |     |     |     | 520 |     |     |     |     | 525 |     |     |     |      |

```
CTG GCG CCC ACC TTG TAC TAACCCCCAC CAGTTCCAGG TCTCGGGATT               4429
Leu Ala Pro Thr Leu Tyr
        530

TCCCGCTCTC CTGCCCAAAA CCTCCCAGCT CAGGCCCTAC CGGAGCTACC ACCTCAGAGT       4489

CCCCACCCCG AAGTGCTATC CTAGCTGCCA CTCCTGCAGA CCCGACCCGG CCCCACCACC       4549

AGAGTTTCAC CTCCCAGCAG TGATTCACAT TCCAGCATTG AAGGAGCCTC AGCTAACAGC       4609

CCTTCAAGGC CCAGCCTATA CCGGAGGCTG AGGCTCTGAT TTCCCTGTGA CACGCGTAGA       4669

CCTACTGCCC GACCCCAACT TCGGTGGCTT GGGATTTTGT GTTCTGCCAC CCTGAACCTC       4729

AGTAAGGGGG CTCGGACCAT CCAGACTGCC CCTACTGCCC ACAGCCACC TGAGGACAAA        4789

GCTGGCACGG TCCCAGGGGT CCCAGGCCCG GCTGGAACCC ACACCTTGCC TTCAGCGACC       4849

TGGACTCTGG GTTCGGAGAG TGGCTTCGGG AGGCGTGGTT TCCGATGGGC GTGCTCTGGA       4909

ACGTGCTCGC CTGAACCAAC CTGTGTACAC TGGCCAGGAA TCACGGCCAC CAGAGCTCGG       4969

ACCTGACAGA GCCCTCAGCA GCCCTCCTA GACCAACGTA CCCATTACAG AGAGGAGACA       5029

GTGACACAGA GGAGAGGAGA CTTGTCCAG GTCCCTCAGC TGCTGTGAGG GCGGCCCTGG       5089

TGCCCCTTCC AGGCTGGGCA TCCCAGTAGC AGCAGGGGAC CCGGGGGTGG GGACACAGGC       5149

CCCGCCCTCC CTGGGAGGCA GGAAGCAGCT CTCAAATAAA CTGTTCTAAG TATGATACAG       5209

GAGTGATACA TGTGTGAAGA GAAGCCCTTA GGTGGGGGCA CAGAGTGTCT GGGTGAGGGG       5269

GGTCAGGGTC ACATCAGGAG GTTAGGGAGG GGTTGATGAA GGGCTGACGT TGAGCAAAGA       5329

CCAAAGGCAA CTCAGAAGGA CAGTGGTGCA GGACTGGGTG TGGTCAGCAG GGGGACTGGT       5389
```

TGGGGGATCC                                                                                      5399

( 2 ) INFORMATION FOR SEQ ID NO:10:

( i ) SEQUENCE CHARACTERISTICS:
        ( A ) LENGTH: 533 amino acids
        ( B ) TYPE: amino acid
        ( D ) TOPOLOGY: linear ( x i ) SEQUENCE DESCRIPTION: SEQ ID NO:10:

```
Met Gln Gly Ala Cys Val Leu Leu Leu Gly Leu His Leu Gln Leu
 1               5                  10                  15

Ser Leu Gly Leu Val Pro Val Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Ala Arg Tyr Asn Gln Cys Lys Thr Thr Arg
    130                 135                 140

Gly Asn Glu Val Thr Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Met Asn Gly Cys Gln Asp Ile Ala Ala Gln
        195                 200                 205

Leu Val Asn Asn Met Asp Ile Asp Val Ile Leu Gly Gly Gly Arg Lys
    210                 215                 220

Tyr Met Phe Pro Val Gly Thr Pro Asp Pro Glu Tyr Pro Asp Asp Ala
225                 230                 235                 240

Ser Val Asn Gly Val Arg Lys Arg Lys Gln Asn Leu Val Gln Ala Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
        275                 280                 285

Glu Pro Ala Asp Met Lys Tyr Asn Val Gln Gln Asp His Thr Lys Asp
    290                 295                 300

Pro Thr Leu Gln Glu Met Thr Glu Val Ala Leu Arg Val Val Ser Arg
305                 310                 315                 320

Asn Pro Arg Gly Phe Tyr Leu Phe Val Glu Gly Gly Arg Ile Asp His
                325                 330                 335

Gly His His Asp Asp Lys Ala Tyr Met Ala Leu Thr Glu Ala Gly Met
            340                 345                 350

Phe Asp Asn Ala Ile Ala Lys Ala Asn Glu Leu Thr Ser Glu Leu Asp
```

```
                     355                      360                      365
        Thr  Leu  Ile  Leu  Val  Thr  Ala  Asp  His  Ser  His  Val  Phe  Ser  Phe  Gly
             370                      375                      380

Gly  Tyr  Thr  Leu  Arg  Gly  Thr  Ser  Ile  Phe  Gly  Leu  Ala  Pro  Ser  Lys
        385                      390                      395                      400

Ala  Leu  Asp  Ser  Lys  Ser  Tyr  Thr  Ser  Ile  Leu  Tyr  Gly  Asn  Gly  Pro
                            405                      410                      415

Gly  Tyr  Ala  Leu  Gly  Gly  Gly  Ser  Arg  Pro  Asp  Val  Asn  Asp  Ser  Thr
                       420                      425                      430

Ser  Glu  Asp  Pro  Ser  Tyr  Gln  Gln  Gln  Ala  Ala  Val  Pro  Gln  Ala  Ser
                  435                      440                      445

Glu  Thr  His  Gly  Gly  Glu  Asp  Val  Ala  Val  Phe  Ala  Arg  Gly  Pro  Gln
                  450                      455                      460

Ala  His  Leu  Val  His  Gly  Val  Glu  Glu  Glu  Thr  Phe  Val  Ala  His  Ile
        465                      470                      475                      480

Met  Ala  Phe  Ala  Gly  Cys  Val  Glu  Pro  Tyr  Thr  Asp  Cys  Asn  Leu  Pro
                            485                      490                      495

Ala  Pro  Thr  Thr  Ala  Thr  Ser  Ile  Pro  Asp  Ala  Ala  His  Leu  Ala  Ala
                       500                      505                      510

Ser  Pro  Pro  Pro  Leu  Ala  Leu  Leu  Ala  Gly  Ala  Met  Leu  Leu  Leu  Leu
                  515                      520                      525

Ala  Pro  Thr  Leu  Tyr
                  530
```

(2) INFORMATION FOR SEQ ID NO:11:

(i) SEQUENCE CHARACTERISTICS:
        (A) LENGTH: 540 amino acids
        (B) TYPE: amino acid
        (D) TOPOLOGY: linear (xi) SEQUENCE DESCRIPTION: SEQ ID NO:11:

```
        Met  Gln  Gly  Asp  Trp  Val  Leu  Leu  Leu  Leu  Gly  Leu  Arg  Ile  His
        1                 5                      10                      15

Leu  Ser  Phe  Gly  Val  Ile  Pro  Val  Glu  Glu  Asn  Pro  Val  Phe  Trp
                       20                      25                      30

Asn  Gln  Lys  Ala  Lys  Glu  Ala  Leu  Asp  Val  Ala  Lys  Lys  Leu  Gln  Pro
                  35                      40                      45

Ile  Gln  Thr  Ser  Ala  Lys  Asn  Leu  Ile  Leu  Phe  Leu  Gly  Asp  Gly  Met
             50                      55                      60

Gly  Val  Pro  Thr  Val  Thr  Ala  Thr  Arg  Ile  Leu  Lys  Gly  Gln  Leu  Gly
        65                      70                      75                      80

Gly  His  Leu  Gly  Pro  Glu  Thr  Pro  Leu  Ala  Met  Asp  His  Phe  Pro  Phe
                            85                      90                      95

Thr  Ala  Leu  Ser  Lys  Thr  Tyr  Asn  Val  Asp  Arg  Gln  Val  Pro  Asp  Ser
                       100                     105                     110

Ala  Gly  Thr  Ala  Thr  Ala  Tyr  Leu  Cys  Gly  Val  Lys  Ala  Asn  Tyr  Lys
                  115                     120                     125

Thr  Ile  Gly  Val  Ser  Ala  Ala  Ala  Arg  Phe  Asn  Gln  Cys  Asn  Ser  Thr
             130                     135                     140

Phe  Gly  Asn  Glu  Val  Phe  Ser  Val  Met  His  Arg  Ala  Lys  Lys  Ala  Gly
        145                     150                     155                     160

Lys  Ser  Val  Gly  Val  Val  Thr  Thr  Thr  Arg  Val  Gln  His  Ala  Ser  Pro
                            165                     170                     175

Ala  Gly  Thr  Tyr  Ala  His  Thr  Val  Asn  Arg  Asp  Trp  Tyr  Ser  Asp  Ala
                       180                     185                     190
```

```
Asp  Met  Pro  Ser  Ser  Ala  Leu  Gln  Glu  Gly  Cys  Lys  Asp  Ile  Ala  Thr
          195                      200                     205

Gln  Leu  Ile  Ser  Asn  Met  Asp  Ile  Asp  Val  Ile  Leu  Gly  Gly  Gly  Arg
     210                      215                     220

Lys  Phe  Met  Phe  Pro  Lys  Gly  Thr  Pro  Asp  Pro  Glu  Tyr  Pro  Gly  Asp
225                           230                     235                      240

Ser  Asp  Gln  Ser  Gly  Val  Arg  Leu  Asp  Ser  Arg  Asn  Leu  Val  Glu  Glu
                    245                      250                     255

Trp  Leu  Ala  Lys  Tyr  Gln  Gly  Thr  Arg  Tyr  Val  Trp  Asn  Arg  Glu  Gln
               260                      265                     270

Leu  Met  Gln  Ala  Ser  Gln  Asp  Pro  Ala  Val  Thr  Arg  Leu  Met  Gly  Leu
          275                      280                     285

Phe  Glu  Pro  Thr  Glu  Met  Lys  Tyr  Asp  Val  Asn  Arg  Asn  Ala  Ser  Ala
     290                      295                     300

Asp  Pro  Ser  Leu  Ala  Glu  Met  Thr  Glu  Val  Ala  Val  Arg  Leu  Leu  Ser
305                           310                     315                      320

Arg  Asn  Pro  Gln  Gly  Phe  Tyr  Leu  Phe  Val  Glu  Gly  Gly  Arg  Ile  Asp
                    325                      330                     335

Gln  Gly  His  His  Ala  Gly  Thr  Ala  Tyr  Leu  Ala  Leu  Thr  Glu  Ala  Val
               340                      345                     350

Met  Phe  Asp  Ser  Ala  Ile  Glu  Lys  Ala  Ser  Gln  Leu  Thr  Asn  Glu  Lys
          355                      360                     365

Asp  Thr  Leu  Thr  Leu  Ile  Thr  Ala  Asp  His  Ser  His  Val  Phe  Ala  Phe
     370                      375                     380

Gly  Gly  Tyr  Thr  Leu  Arg  Gly  Thr  Ser  Ile  Phe  Gly  Leu  Ala  Pro  Leu
385                           390                     395                      400

Asn  Ala  Gln  Asp  Gly  Lys  Ser  Tyr  Thr  Ser  Ile  Leu  Tyr  Gly  Asn  Gly
                    405                      410                     415

Pro  Gly  Tyr  Val  Leu  Asn  Ser  Gly  Asn  Arg  Pro  Asn  Val  Thr  Asp  Ala
               420                      425                     430

Glu  Ser  Gly  Asp  Val  Asn  Tyr  Lys  Gln  Gln  Ala  Ala  Val  Pro  Leu  Ser
          435                      440                     445

Ser  Glu  Thr  His  Gly  Gly  Glu  Asp  Val  Ala  Ile  Phe  Ala  Arg  Gly  Pro
     450                      455                     460

Gln  Ala  His  Leu  Val  His  Gly  Val  Gln  Glu  Gln  Asn  Tyr  Ile  Ala  His
465                           470                     475                      480

Val  Met  Ala  Phe  Ala  Gly  Cys  Leu  Glu  Pro  Tyr  Thr  Asp  Cys  Gly  Leu
                    485                      490                     495

Ala  Pro  Pro  Ala  Asp  Glu  Asn  Arg  Pro  Thr  Thr  Pro  Val  Gln  Asn  Ser
               500                      505                     510

Ala  Ile  Thr  Met  Asn  Asn  Val  Leu  Leu  Ser  Leu  Gln  Leu  Leu  Val  Ser
          515                      520                     525

Met  Leu  Leu  Leu  Val  Gly  Thr  Ala  Leu  Val  Val  Ser
          530                      535                     540
```

( 2 ) INFORMATION FOR SEQ ID NO:12:

( i ) SEQUENCE CHARACTERISTICS:
        ( A ) LENGTH: 559 amino acids
        ( B ) TYPE: amino acid
        ( D ) TOPOLOGY: linear ( x i ) SEQUENCE DESCRIPTION: SEQ ID NO:12:

```
Met  Gln  Gly  Pro  Trp  Val  Leu  Leu  Leu  Leu  Gly  Leu  Arg  Leu  Gln  Leu
1                   5                        10                      15
```

-continued

```
Ser Leu Ser Val Ile Pro Val Glu Glu Asn Pro Ala Phe Trp Asn
         20              25              30

Lys Lys Ala Ala Glu Ala Leu Asp Ala Ala Lys Lys Leu Gln Pro Ile
         35              40              45

Gln Thr Ser Ala Lys Asn Leu Ile Ile Phe Leu Gly Asp Gly Met Gly
     50              55              60

Val Pro Thr Val Thr Ala Thr Arg Ile Leu Lys Gly Gln Leu Glu Gly
65              70              75              80

His Leu Gly Pro Glu Thr Pro Leu Ala Met Asp Arg Phe Pro Tyr Met
             85              90              95

Ala Leu Ser Lys Thr Tyr Ser Val Asp Arg Gln Val Pro Asp Ser Ala
         100             105             110

Ser Thr Ala Thr Ala Tyr Leu Cys Gly Val Lys Thr Asn Tyr Lys Thr
         115             120             125

Ile Gly Leu Ser Ala Ala Ala Arg Phe Asp Gln Cys Asn Thr Thr Phe
         130             135             140

Gly Asn Glu Val Phe Ser Val Met Tyr Arg Ala Lys Lys Ala Gly Lys
145             150             155             160

Ser Val Gly Val Val Thr Thr Thr Arg Val Gln His Ala Ser Pro Ser
             165             170             175

Gly Thr Tyr Val His Thr Val Asn Arg Asn Trp Tyr Gly Asp Ala Asp
             180             185             190

Met Pro Ala Ser Ala Leu Arg Glu Gly Cys Lys Asp Ile Ala Thr Gln
         195             200             205

Leu Ile Ser Asn Met Asp Ile Asn Val Ile Leu Gly Gly Gly Arg Lys
     210             215             220

Tyr Met Phe Pro Ala Gly Thr Pro Asp Pro Glu Tyr Pro Asn Asp Ala
225             230             235             240

Asn Glu Thr Gly Thr Arg Leu Asp Gly Arg Asn Leu Val Gln Glu Trp
             245             250             255

Leu Ser Lys His Gln Gly Ser Gln Tyr Val Trp Asn Arg Glu Gln Leu
             260             265             270

Ile Gln Lys Ala Gln Asp Pro Ser Val Thr Tyr Leu Met Gly Leu Phe
         275             280             285

Glu Pro Val Asp Thr Lys Phe Asp Ile Gln Arg Asp Pro Leu Met Asp
     290             295             300

Pro Ser Leu Lys Asp Met Thr Glu Thr Ala Val Lys Val Leu Ser Arg
305             310             315             320

Asn Pro Lys Gly Phe Tyr Leu Phe Val Glu Gly Gly Arg Ile Asp Arg
             325             330             335

Gly His His Leu Gly Thr Ala Tyr Leu Ala Leu Thr Glu Ala Val Met
             340             345             350

Phe Asp Leu Ala Ile Glu Arg Ala Ser Gln Leu Thr Ser Glu Arg Asp
         355             360             365

Thr Leu Thr Ile Val Thr Ala Asp His Ser His Val Phe Ser Phe Gly
     370             375             380

Gly Tyr Thr Leu Arg Gly Thr Ser Ile Phe Gly Leu Ala Pro Leu Asn
385             390             395             400

Ala Leu Asp Gly Lys Pro Tyr Thr Ser Ile Leu Tyr Gly Asn Gly Pro
             405             410             415

Gly Tyr Val Gly Gly Thr Gly Glu Arg Pro Asn Val Thr Ala Ala Glu
             420             425             430

Ser Ser Gly Ser Ser Tyr Arg Arg Gln Ala Ala Val Pro Val Lys Ser
         435             440             445
```

```
Glu  Thr  His  Gly  Gly  Glu  Asp  Val  Ala  Ile  Phe  Ala  Arg  Gly  Pro  Gln
     450                 455                      460

Ala  His  Leu  Val  His  Gly  Val  Gln  Glu  Gln  Asn  Tyr  Ile  Ala  His  Val
465                      470                 475                           480

Met  Ala  Ser  Ala  Gly  Cys  Leu  Glu  Pro  Tyr  Thr  Asp  Cys  Gly  Leu  Ala
               485                      490                           495

Pro  Pro  Ala  Asp  Glu  Ser  Gln  Thr  Thr  Thr  Thr  Thr  Arg  Gln  Thr  Thr
               500                 505                      510

Ile  Thr  Thr  Thr  Thr  Thr  Thr  Thr  Thr  Thr  Thr  Thr  Thr  Pro  Val  His
          515                 520                      525

Asn  Ser  Ala  Arg  Ser  Leu  Gly  Pro  Ala  Thr  Ala  Pro  Leu  Ala  Leu  Ala
     530                 535                      540

Leu  Leu  Ala  Gly  Met  Leu  Met  Leu  Leu  Leu  Gly  Ala  Pro  Ala  Glu
545                 550                      555
```

(2) INFORMATION FOR SEQ ID NO:13:

(i) SEQUENCE CHARACTERISTICS:
      (A) LENGTH: 528 amino acids
      (B) TYPE: amino acid
      (D) TOPOLOGY: linear (xi) SEQUENCE DESCRIPTION: SEQ ID NO:13:

```
Met  Gln  Gly  Pro  Trp  Val  Leu  Leu  Leu  Gly  Leu  Arg  Leu  Gln  Leu
1                   5                   10                       15

Ser  Leu  Gly  Val  Ile  Pro  Ala  Glu  Glu  Asn  Pro  Ala  Phe  Trp  Asn
               20                  25                       30

Arg  Gln  Ala  Ala  Glu  Ala  Leu  Asp  Ala  Ala  Lys  Lys  Leu  Gln  Pro  Ile
               35                  40                       45

Gln  Lys  Val  Ala  Lys  Asn  Leu  Ile  Leu  Phe  Leu  Gly  Asp  Gly  Leu  Gly
     50                       55                       60

Val  Pro  Thr  Val  Thr  Ala  Thr  Arg  Ile  Leu  Lys  Gly  Gln  Lys  Asn  Gly
65                       70                       75                       80

Lys  Leu  Gly  Pro  Glu  Thr  Pro  Leu  Ala  Met  Asp  Arg  Phe  Pro  Tyr  Leu
               85                       90                       95

Ala  Leu  Ser  Lys  Thr  Tyr  Asn  Val  Asp  Arg  Gln  Val  Pro  Asp  Ser  Ala
               100                      105                      110

Ala  Thr  Ala  Thr  Ala  Tyr  Leu  Cys  Gly  Val  Lys  Ala  Asn  Phe  Gln  Thr
               115                      120                      125

Ile  Gly  Leu  Ser  Ala  Ala  Ala  Arg  Phe  Asn  Gln  Cys  Asn  Thr  Thr  Arg
     130                      135                      140

Gly  Asn  Glu  Val  Ile  Ser  Val  Met  Asn  Arg  Ala  Lys  Gln  Ala  Gly  Lys
145                      150                      155                      160

Ser  Val  Gly  Val  Val  Thr  Thr  Thr  Arg  Val  Gln  His  Ala  Ser  Pro  Ala
                    165                      170                      175

Gly  Thr  Tyr  Ala  His  Thr  Val  Asn  Arg  Asn  Trp  Tyr  Ser  Asp  Ala  Asp
               180                      185                      190

Met  Pro  Ala  Ser  Ala  Arg  Gln  Glu  Gly  Cys  Gln  Asp  Ile  Ala  Thr  Gln
          195                      200                      205

Leu  Ile  Ser  Asn  Met  Asp  Ile  Asp  Val  Ile  Leu  Gly  Gly  Gly  Arg  Lys
     210                      215                      220

Tyr  Met  Phe  Pro  Met  Gly  Thr  Pro  Asp  Pro  Glu  Tyr  Pro  Ala  Asp  Ala
225                      230                      235                      240

Ser  Gln  Asn  Gly  Ile  Arg  Leu  Asp  Gly  Lys  Asn  Leu  Val  Gln  Glu  Trp
                    245                      250                      255
```

-continued

| | | | | | | | | | | | | | | |
|---|---|---|---|---|---|---|---|---|---|---|---|---|---|---|
| Leu | Ala | Lys | His 260 | Gln | Gly | Ala | Trp | Tyr 265 | Val | Trp | Asn | Arg | Thr 270 | Glu | Leu |
| Met | Glu | Ala 275 | Ser | Leu | Asp | Gln | Ser 280 | Val | Thr | His | Leu | Met 285 | Gly | Leu | Phe |
| Glu | Pro 290 | Gly | Asp | Thr | Lys | Tyr 295 | Glu | Ile | His | Arg | Asp 300 | Pro | Thr | Leu | Asp |
| Pro 305 | Ser | Leu | Met | Glu | Met 310 | Thr | Glu | Ala | Ala | Leu 315 | Arg | Leu | Leu | Ser | Arg 320 |
| Asn | Pro | Arg | Gly | Phe 325 | Tyr | Leu | Phe | Val | Glu 330 | Gly | Gly | Arg | Ile | Asp 335 | His |
| Gly | His | His | Glu 340 | Gly | Val | Ala | Tyr | Gln 345 | Ala | Leu | Thr | Glu | Ala 350 | Val | Met |
| Phe | Asp | Asp 355 | Ala | Ile | Glu | Arg | Ala 360 | Gly | Gln | Leu | Thr | Ser 365 | Glu | Glu | Asp |
| Thr | Leu 370 | Thr | Leu | Val | Thr | Ala 375 | Asp | His | Ser | His | Val 380 | Phe | Ser | Phe | Gly |
| Gly 385 | Tyr | Thr | Leu | Arg | Gly 390 | Ser | Ser | Ile | Phe | Gly 395 | Leu | Ala | Pro | Ser | Lys 400 |
| Ala | Gln | Asp | Ser | Lys 405 | Ala | Tyr | Thr | Ser | Thr 410 | Leu | Tyr | Gly | Asn | Gly 415 | Pro |
| Gly | Tyr | Val | Phe 420 | Asn | Ser | Gly | Val | Arg 425 | Pro | Asp | Val | Asn | Glu 430 | Ser | Glu |
| Ser | Gly | Ser 435 | Pro | Asp | Tyr | Gln | Gln 440 | Gln | Ala | Ala | Val | Pro 445 | Leu | Ser | Ser |
| Glu | Thr 450 | His | Gly | Gly | Glu | Asp 455 | Val | Ala | Val | Phe | Ala 460 | Arg | Gly | Pro | Gln |
| Ala 465 | His | Leu | Val | His | Gly 470 | Val | Gln | Glu | Gln | Ser 475 | Phe | Val | Ala | His | Val 480 |
| Met | Ala | Phe | Ala | Ala 485 | Cys | Leu | Glu | Pro | Tyr 490 | Thr | Ala | Cys | Asp | Leu 495 | Ala |
| Pro | Pro | Ala | Cys 500 | Thr | Thr | Asp | Ala | Ala 505 | His | Pro | Val | Ala | Ala 510 | Ser | Leu |
| Pro | Leu | Leu 515 | Ala | Gly | Thr | Leu | Leu 520 | Leu | Leu | Gly | Ala | Ser 525 | Ala | Ala | Pro |